United States Patent
Sellers et al.

(10) Patent No.: US 7,273,591 B2
(45) Date of Patent: Sep. 25, 2007

(54) SLIDE CARTRIDGE AND REAGENT TEST SLIDES FOR USE WITH A CHEMICAL ANALYZER, AND CHEMICAL ANALYZER FOR SAME

(75) Inventors: James M. Sellers, Newburyport, MA (US); Haydn B. Taylor, Nashua, NH (US); Lawrence M. Kuba, Nashua, NH (US)

(73) Assignee: IDEXX Laboratories, Inc., Westbrook, MA (US)

( * ) Notice: Subject to any disclaimer, the term of this patent is extended or adjusted under 35 U.S.C. 154(b) by 795 days.

(21) Appl. No.: 10/639,031

(22) Filed: Aug. 12, 2003

(65) Prior Publication Data

US 2005/0036911 A1  Feb. 17, 2005

(51) Int. Cl.
   *B01L 3/00*   (2006.01)
(52) U.S. Cl. .......................... 422/104; 422/58; 422/64; 422/99; 422/102
(58) Field of Classification Search .......... 422/99–100, 422/102, 104, 58, 64, 68.1
   See application file for complete search history.

(56) References Cited

U.S. PATENT DOCUMENTS

| | | |
|---|---|---|
| 2,058,516 A | 10/1936 | Schaaff |
| 2,204,471 A | 6/1940 | Campbell, Jr. et al. |
| 2,363,474 A | 11/1944 | Schlesinger |
| 2,586,513 A | 2/1952 | Butler |
| 2,598,869 A | 6/1952 | White |
| 2,665,825 A | 1/1954 | Poitras et al. |
| 2,692,820 A | 10/1954 | Alway et al. |
| 2,721,008 A | 10/1955 | Morgan, Jr. |
| 2,797,149 A | 6/1957 | Skeggs |
| 2,802,605 A | 8/1957 | Parker |
| 3,036,893 A | 5/1962 | Natelson |
| 3,106,845 A | 10/1963 | Dimmick |
| 3,164,304 A | 1/1965 | Jager et al. |
| 3,190,731 A | 6/1965 | Weiskopf |
| 3,300,099 A | 1/1967 | Marona |
| 3,323,689 A | 6/1967 | Elmore |
| 3,341,087 A | 9/1967 | Rosin et al. |
| 3,367,746 A | 2/1968 | Maurukas |
| 3,449,081 A | 6/1969 | Hughes |
| 3,460,529 A | 8/1969 | Leucci |
| 3,526,480 A | 9/1970 | Findl et al. |
| 3,533,744 A | 10/1970 | Unger |

(Continued)

*Primary Examiner*—Brian R. Gordon
(74) *Attorney, Agent, or Firm*—Gerald T. Bodner

(57) ABSTRACT

A slide cartridge for use with a chemical analyzer includes an upper ring and a lower ring secured together but rotatable with respect to each other. The upper and lower rings define a plurality of reaction chambers between them, which receive dry analyte test slides. A gear track formed in the underside of the lower ring engages a pinion gear attached to a stepping motor of the chemical analyzer in order to rotate the slide cartridge. The slide cartridge is rotated under a sample fluid metering device, which deposits a sample fluid on the test slides through a plurality of spotter ports formed in the upper ring, and above a reflectometer, which performs a colorimetric measurement on the spotted test slides through viewing windows formed in the lower ring of the slide cartridge. A chemical analyzer with which the slide cartridge may be used includes a reflectometer, a sample fluid metering device and a stepping motor for rotating the slide cartridge.

21 Claims, 14 Drawing Sheets

U.S. PATENT DOCUMENTS

| | | |
|---|---|---|
| 3,572,400 A | 3/1971 | Casner et al. |
| 3,574,064 A | 4/1971 | Binnings et al. |
| 3,615,240 A | 10/1971 | Sanz |
| 3,616,264 A | 10/1971 | Ray et al. |
| 3,618,829 A | 11/1971 | Elmore et al. |
| 3,645,423 A | 2/1972 | DeGraw |
| 3,650,437 A | 3/1972 | Binnings et al. |
| 3,659,934 A | 5/1972 | Costanza et al. |
| 3,675,488 A | 7/1972 | Viktora et al. |
| 3,748,044 A | 7/1973 | Liston |
| 3,754,866 A | 8/1973 | Ritchie et al. |
| 3,756,920 A | 9/1973 | Kelbaugh et al. |
| 3,758,274 A | 9/1973 | Ritchie et al. |
| 3,788,816 A | 1/1974 | Rohrbaugh et al. |
| 3,790,346 A | 2/1974 | Ritchie |
| 3,810,779 A | 5/1974 | Pickett et al. |
| 3,832,135 A | 8/1974 | Drozdowski et al. |
| 3,855,867 A | 12/1974 | Roach |
| 3,856,470 A | 12/1974 | Cullis et al. |
| 3,873,273 A | 3/1975 | Moran et al. |
| 3,883,308 A | 5/1975 | Matte |
| 3,904,372 A | 9/1975 | Lightner |
| 3,915,651 A | 10/1975 | Nishi |
| 3,918,913 A | 11/1975 | Stevenson et al. |
| 3,926,514 A | 12/1975 | Costanza et al. |
| 3,942,952 A | 3/1976 | Atwood |
| 4,041,995 A | 8/1977 | Columbus |
| 4,043,756 A | 8/1977 | Sommervold |
| 4,052,161 A | 10/1977 | Atwood et al. |
| 4,059,405 A | 11/1977 | Sodickson et al. |
| 4,061,469 A | 12/1977 | DuBose |
| 4,067,694 A | 1/1978 | Blakely et al. |
| 4,090,791 A | 5/1978 | Siddiqi et al. |
| 4,119,381 A | 10/1978 | Muka et al. |
| 4,142,656 A | 3/1979 | Smith et al. |
| 4,152,390 A | 5/1979 | Nosco et al. |
| 4,160,646 A | 7/1979 | Furutani et al. |
| 4,161,508 A | 7/1979 | Jänchen |
| 4,198,483 A | 4/1980 | Sogi et al. |
| 4,198,485 A | 4/1980 | Stark, Jr. |
| 4,210,724 A | 7/1980 | Sogi et al. |
| 4,219,529 A | 8/1980 | Tersteeg et al. |
| 4,224,032 A | 9/1980 | Glover et al. |
| 4,234,538 A | 11/1980 | Ginsberg et al. |
| 4,234,539 A | 11/1980 | Ginsberg et al. |
| 4,236,894 A | 12/1980 | Sommervold |
| 4,264,560 A | 4/1981 | Natelson |
| 4,271,123 A | 6/1981 | Curry et al. |
| 4,272,482 A | 6/1981 | Jessop et al. |
| 4,277,440 A | 7/1981 | Jessop et al. |
| 4,287,155 A | 9/1981 | Tersteeg et al. |
| 4,296,069 A | 10/1981 | Smith et al. |
| 4,296,070 A | 10/1981 | Montalto et al. |
| 4,298,571 A | 11/1981 | DiFulvio et al. |
| 4,298,575 A | 11/1981 | Berglund |
| 4,302,420 A | 11/1981 | Jakubowicz et al. |
| 4,303,611 A | 12/1981 | Jessop |
| 4,308,231 A | 12/1981 | Kolber et al. |
| 4,321,122 A | 3/1982 | Whitcomb et al. |
| 4,325,909 A | 4/1982 | Coulter et al. |
| 4,335,620 A | 6/1982 | Adams |
| 4,340,390 A | 7/1982 | Collins et al. |
| 4,347,750 A | 9/1982 | Tersteeg et al. |
| 4,351,799 A | 9/1982 | Gross et al. |
| 4,359,447 A | 11/1982 | Welch |
| 4,387,990 A * | 6/1983 | Yazawa et al. ............. 356/244 |
| 4,392,195 A | 7/1983 | Inoue |
| 4,399,711 A | 8/1983 | Klein |
| 4,420,566 A | 12/1983 | Jessop et al. |
| 4,424,191 A | 1/1984 | Jakubowicz |
| 4,429,373 A | 1/1984 | Fletcher et al. |
| 4,430,299 A | 2/1984 | Horne |
| 4,441,532 A | 4/1984 | Hrubesh |
| 4,451,433 A | 5/1984 | Yamashita et al. |
| 4,452,899 A | 6/1984 | Alston |
| 4,455,280 A | 6/1984 | Shinohara et al. |
| 4,475,666 A | 10/1984 | Bilbrey et al. |
| 4,488,810 A | 12/1984 | Hatanaka et al. |
| 4,503,011 A | 3/1985 | Hubeau |
| 4,512,952 A | 4/1985 | Blanding et al. |
| 4,522,921 A | 6/1985 | Ogawa |
| 4,539,855 A | 9/1985 | Jacobs |
| 4,540,549 A | 9/1985 | Manabe |
| 4,549,809 A | 10/1985 | Minekane et al. |
| D282,203 S | 1/1986 | Leonard et al. |
| 4,568,519 A | 2/1986 | Hamilton et al. |
| 4,584,275 A | 4/1986 | Okano et al. |
| 4,599,219 A | 7/1986 | Cooper et al. |
| 4,615,360 A | 10/1986 | Jacobs |
| 4,627,014 A | 12/1986 | Lo et al. |
| 4,629,703 A | 12/1986 | Uffenheimer |
| 4,644,807 A | 2/1987 | Mar |
| 4,647,431 A | 3/1987 | Sekine et al. |
| 4,656,006 A | 4/1987 | Assmann et al. |
| 4,656,007 A | 4/1987 | Douchy et al. |
| 4,670,219 A | 6/1987 | Nelson et al. |
| 4,675,301 A | 6/1987 | Charneski et al. |
| 4,678,755 A | 7/1987 | Shinohara et al. |
| 4,680,164 A | 7/1987 | Kelln |
| 4,681,741 A | 7/1987 | Hanaway |
| 4,695,430 A | 9/1987 | Coville et al. |
| 4,706,207 A | 11/1987 | Hennessy et al. |
| 4,710,352 A | 12/1987 | Slater et al. |
| 4,713,974 A | 12/1987 | Stone |
| 4,719,085 A | 1/1988 | Jacobs |
| 4,731,058 A | 3/1988 | Doan |
| 4,737,344 A | 4/1988 | Koizumi et al. |
| 4,738,826 A | 4/1988 | Harris |
| 4,752,449 A | 6/1988 | Jackson et al. |
| 4,757,449 A | 7/1988 | Kurihara et al. |
| 4,761,268 A | 8/1988 | Andersen et al. |
| 4,769,009 A | 9/1988 | Dykstra |
| 4,770,053 A | 9/1988 | Broderick et al. |
| 4,774,055 A | 9/1988 | Wakatake et al. |
| 4,785,407 A | 11/1988 | Sakagami |
| 4,794,085 A | 12/1988 | Jessop et al. |
| 4,798,705 A | 1/1989 | Jakubowicz et al. |
| 4,808,380 A | 2/1989 | Minekane |
| 4,814,279 A | 3/1989 | Sugaya |
| 4,821,586 A | 4/1989 | Scordato et al. |
| 4,823,992 A | 4/1989 | Fiorentini |
| 4,826,659 A | 5/1989 | Akisada |
| 4,837,159 A | 6/1989 | Yamada |
| 4,841,208 A | 6/1989 | Itoh |
| 4,855,109 A | 8/1989 | Muraishi et al. |
| 4,863,695 A | 9/1989 | Fullemann |
| 4,935,374 A | 6/1990 | Jacobs et al. |
| 4,943,415 A | 7/1990 | Przybylowicz et al. |
| 5,034,191 A | 7/1991 | Porte |
| 5,037,613 A | 8/1991 | Shaw et al. |
| 5,075,079 A * | 12/1991 | Kerr et al. ............. 422/64 |
| 5,089,229 A | 2/1992 | Heidt et al. |
| 5,102,624 A | 4/1992 | Muraishi |
| 5,126,952 A | 6/1992 | Kildal-Brandt et al. |
| 5,174,960 A * | 12/1992 | Shaw et al. ............. 422/63 |
| 5,250,262 A | 10/1993 | Heidt et al. |
| 5,257,212 A | 10/1993 | Kildal-Brandt et al. |
| 5,283,195 A * | 2/1994 | Muszak et al. ............. 436/48 |
| 5,304,350 A | 4/1994 | Meserol ............. 422/104 |
| 5,336,467 A | 8/1994 | Heidt et al. |
| 5,425,918 A | 6/1995 | Healey et al. ............. 422/64 |
| 5,525,514 A | 6/1996 | Jacobs et al. ............. 436/46 |
| 5,525,551 A | 6/1996 | Ohta |
| 5,654,200 A * | 8/1997 | Copeland et al. ............. 436/46 |

| | | | |
|---|---|---|---|
| 6,013,528 A | 1/2000 | Jacobs et al. | |
| 6,136,270 A * | 10/2000 | Maes et al. | 422/64 |
| 6,183,693 B1 * | 2/2001 | Bogen et al. | 422/64 |
| 6,268,162 B1 | 7/2001 | Phillips et al. | |
| 6,296,809 B1 * | 10/2001 | Richards et al. | 422/64 |
| 6,352,861 B1 | 3/2002 | Copeland et al. | 436/46 |
| 6,387,326 B1 * | 5/2002 | Edwards et al. | 422/63 |
| 6,531,094 B2 * | 3/2003 | Seto et al. | 422/64 |
| 6,531,095 B2 * | 3/2003 | Hammer et al. | 422/64 |
| 6,783,733 B2 | 8/2004 | Bogen et al. | 422/64 |
| 2003/0022380 A1 | 1/2003 | Jakubowicz et al. | |
| 2003/0104634 A1 | 6/2003 | Jacobs et al. | |
| 2004/0072363 A1 * | 4/2004 | Schembri | 436/174 |
| 2004/0191923 A1 * | 9/2004 | Tomasso et al. | 436/180 |

\* cited by examiner

SLIDE CARTRIDGE AND REAGENT TEST SLIDES FOR USE WITH A CHEMICAL ANALYZER, AND CHEMICAL ANALYZER FOR SAME

BACKGROUND OF THE INVENTION

1. Field of the Invention

This invention relates to chemical analyzers which automatically analyze fluids, and more particularly relates to "dry chemistry" analyzers. Even more specifically, this invention relates to chemical analyzers that are particularly adapted for biological fluid testing purposes wherein a change in an optical characteristic of a sample is sensed and analyzed automatically by the analyzer. The analyzer of the present invention has particular utility for human and veterinary applications.

2. Description of the Prior Art

Various analyzers have been developed for automated test procedures involving essentially dry, analytical elements, which elements offer substantial storage and handling conveniences. The "dry" analytical elements are preferably in the form of test slides. The test slides are formed as a multi-layer element containing the necessary free agents for reaction with components of a biological fluid, such as blood serum, deposited thereon. Certain reactions colorimetrically produce a change in optical density, which is sensed by a reflectometer or other device, the amount of light reflected from the test element varying in accordance with the reaction and being indicative of the amount of a particular component present in the fluid. Such test slides containing a dry analyte are well known in the art and are described in U.S. Pat. No. 4,647,431, which issued to Takasi Sekine, et al. Instruments utilizing dry slides are also known, such as the VETTEST® analyzer available from IDEXX Laboratories, Inc., Westbrook, Me. and the VITROS® analyzer available from Ortho-Clinical Diagnostics, Inc, Rochester, N.Y.

A very capable "dry chemistry" analyzer is described in U.S. Pat. No. 5,089,229, which issued to Thomas Heidt et al., the disclosure of which is incorporated herein by reference. The chemical analyzer described in the aforementioned '229 Heidt et al. patent includes a rotatable turntable which is adapted to hold a plurality of reagent test slides, a sample metering device, an incubator or temperature controller, a reflectometer, a slide injector mechanism, a slide ejector mechanism and associated electronics, computer or microprocessor, and software. The rotatable turntable preferably holds up to 12 slides about its circumference. The test slides come individually sealed. They are unsealed and immediately placed in the injector mechanism, which transfers the slides to the rotatable turntable. The turntable positions the reagent test slides under the metering device, which device deposits a predetermined amount of sample onto each slide. The turntable also carries the slides above a reflectometer. After testing has been completed, the ejector mechanism automatically removes the reagent slides from the turntable.

In the chemical analyzer described in the '229 Heidt et al. patent, the rotatable turntable is formed as an integral part of the chemical analyzer. It is not intended to be removed except in the situation where the chemical analyzer needs to be disassembled for repair. The dry analytical test slides come individually prepackaged, and are inserted by the operator onto the rotatable turntable one at a time by using the inserter mechanism. In routine testing of biological fluids, very often the same test slides will be used. There are times when multiple test slides containing the same chemical reagent are used concurrently in the test run, for redundancy, averaging of test results or for verification of test accuracy. Sometimes, for certain fluid tests, the operator may wish to select special reagent test slides not used in routine testing.

OBJECTS AND SUMMARY OF THE INVENTION

It is an object of the present invention to provide a cartridge for carrying pre-loaded reagent test slides for use in a chemical analyzer.

It is another object of the present invention to provide a pre-packaged, sealed storage cartridge for carrying pre-loaded reagent test slides for use in a chemical analyzer.

It is a further object of the present invention to provide a reagent test slide cartridge for use with a chemical analyzer which provides a reaction chamber for the test slides.

It is still another object of the present invention to provide a cartridge for carrying pre-loaded reagent test slides which is receivable by a chemical analyzer and rotatable therein.

It is yet a further object of the present invention to provide a cartridge for captively receiving selected reagent test slides insertable by a user.

It is still another object of the present invention to provide a cartridge for carrying reagent test slides which operates in conjunction with a sample metering device of a chemical analyzer to selectively allow the depositing of metered amounts of a sample fluid onto each test slide carried thereon.

It is a further object of the present invention to provide a cartridge for carrying reagent test slides which operates in conjunction with a reflectometer of a chemical analyzer to selectively allow exposure of the test slides to the reflectometer for colorimetric measurements.

It is still another object of the present invention to provide a cartridge for carrying pre-loaded test slides, which cartridge may be easily and quickly inserted on a chemical analyzer and removed therefrom after completion of tests for disposal.

It is yet a further object of the present invention to provide a chemical analyzer for use in conjunction with a cartridge which carries pre-loaded test slides.

It is still a further object of the present invention to provide reagent test slides receivable by the slide cartridge.

In accordance with one form of the present invention, a slide cartridge for use with a chemical analyzer includes a pair of mating upper and lower rings which are secured together but are at least partially rotatable with respect to one another. They define between them one or more reaction chambers in which dry analyte test slides may reside. The lower ring has a series of openings or viewing windows so that each of the test slides may be exposed to a reflectometer of the chemical analyzer for calorimetric measurements. The upper ring includes a plurality of spotter ports to allow a sample fluid being tested to be deposited on each test slide through the slide cartridge by a sample metering device of the chemical analyzer. The upper ring also has a plurality of reaction chamber caps to selectively cover and uncover the reagent side of the test slides to prevent evaporation of a sample fluid deposited on each test slide.

A chemical analyzer formed in accordance with one form of the present invention receives the slide cartridge with pre-loaded or user-inserted test slides, and includes a reflectometer and sample metering device, as well as associated electronic circuitry and software for analyzer operation. The analyzer rotates the slide cartridge in alignment with the metering device, which deposits a sample fluid to be tested on each slide. It also rotates the slide cartridge in alignment with a reflectometer which conducts measurements on each test slide to determine the colorimetric effect the sample fluid has on the test slide reagent. When analysis is complete, the entire slide cartridge, including the spent test slides carried thereby, is removed by the user and properly discarded.

In accordance further with the present invention, a test slide is particularly structured to be received by, and held captive in, the slide cartridge of the present invention. Preferably, the reagent test slide is trapezoidal in shape, which allows a large number of reagent test slides to be carried by the slide cartridge, thus allowing a slide cartridge with a smaller radius to be used, and facilitates insertion of the test slides by a user without confusion as to orientation.

These and other objects, features, and advantages of the present invention will be apparent from the following detailed description of illustrative embodiments thereof, which is to be read in connection with the accompanying drawings.

DETAILED DESCRIPTION OF THE PREFERRED EMBODIMENTS

Figure 1:
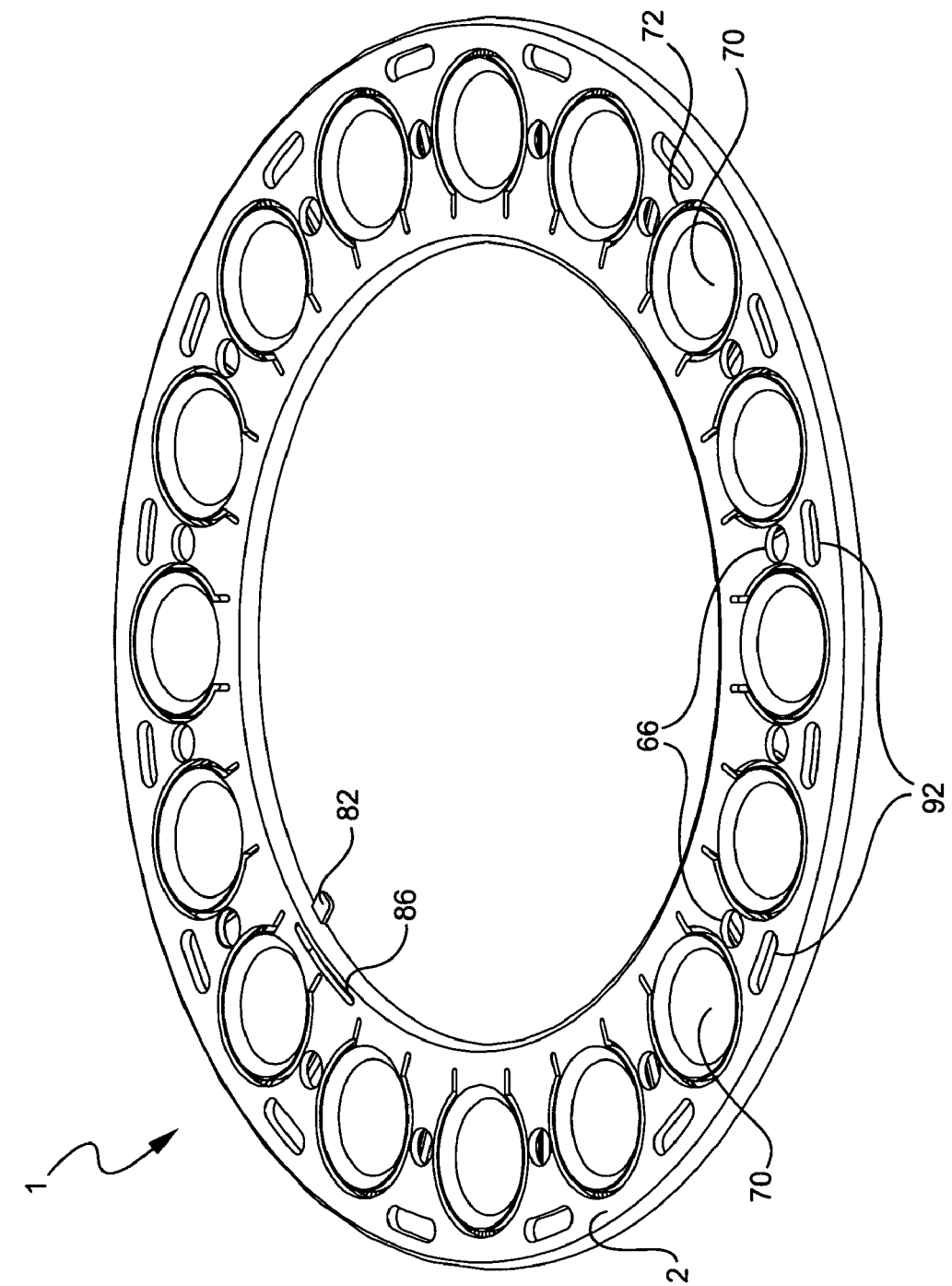
FIG. 1 is a top isometric view of a slide cartridge formed in accordance with one form of the present invention.
Figure 2:
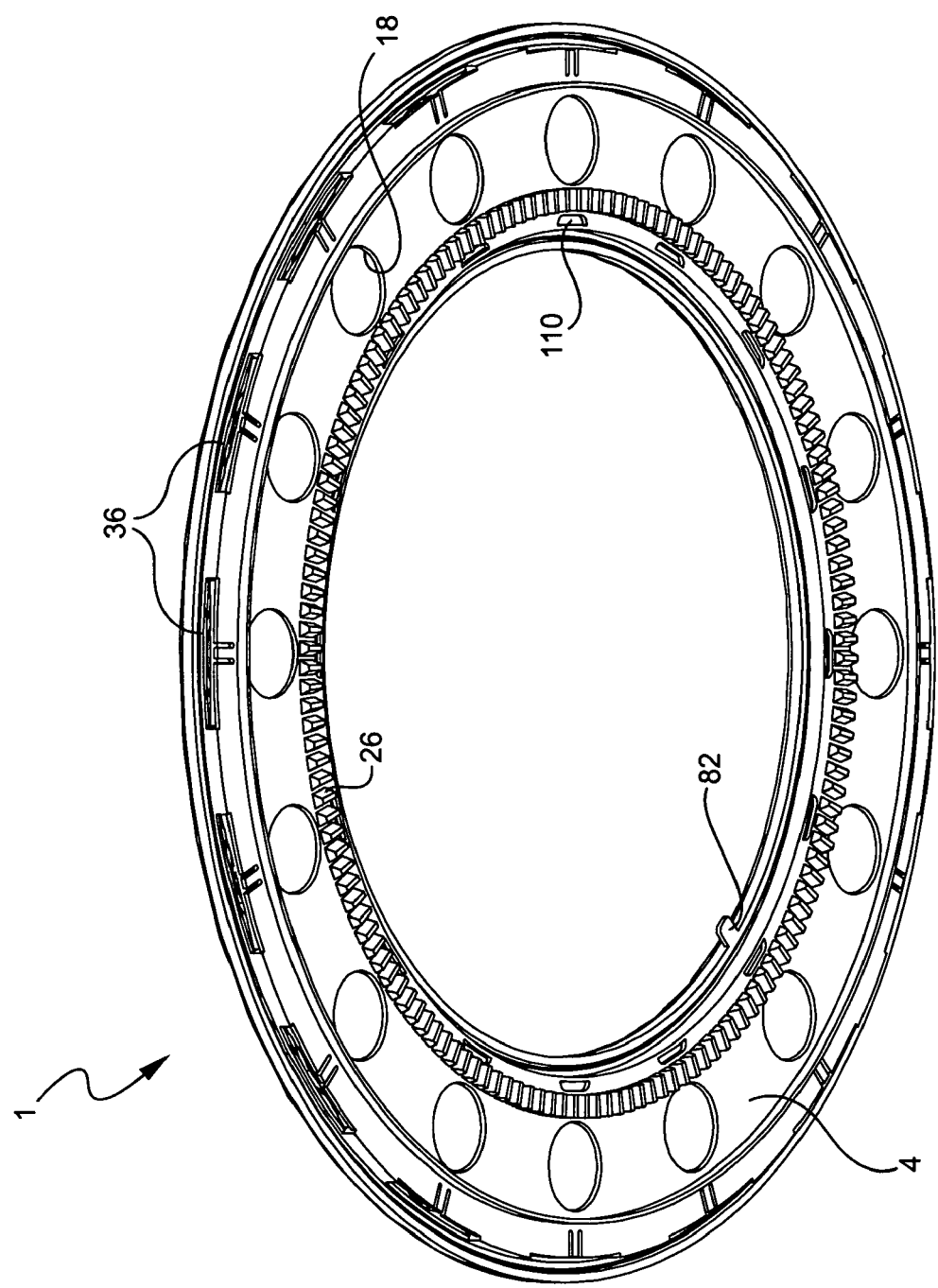
FIG. 2 is a bottom isometric view of the slide cartridge of the present invention shown in FIG. 1.

Referring initially to FIGS. 1-12 of the drawings, it will be seen that a slide cartridge 1 formed in accordance with one form of the present invention for use with a chemical analyzer preferably includes a pair of mating upper and lower rings 2, 4, secured together but at least partially rotatable with respect to each other. As will be described in greater detail, the upper and lower rings 2, 4 define between them a single reaction chamber, or a plurality of individual reaction chambers 6, in which dry analyte test slides 8, similar to those described in the aforementioned Sekine et al. patent, may reside. Rings 2 and 4 can be manufactured from any suitable material such as, for example, plastic, glass, fiber, metal or a combination thereof.

The lower ring 4 acts as a tray for holding a plurality of reagent test slides 8 in a spaced apart relationship circumferentially about the lower ring. It includes a primary or bottom wall 10, and radially spaced apart inner and outer sidewalls 12, 14 (see FIG. 11) extending perpendicularly to the bottom wall 10, in the same direction, and attached to opposite edges of the bottom wall. The radial spacing between the inner and outer sidewalls 12, 14 is preferably slightly greater than the depth of a reagent test slide 8 which is received thereby.

Figure 5:
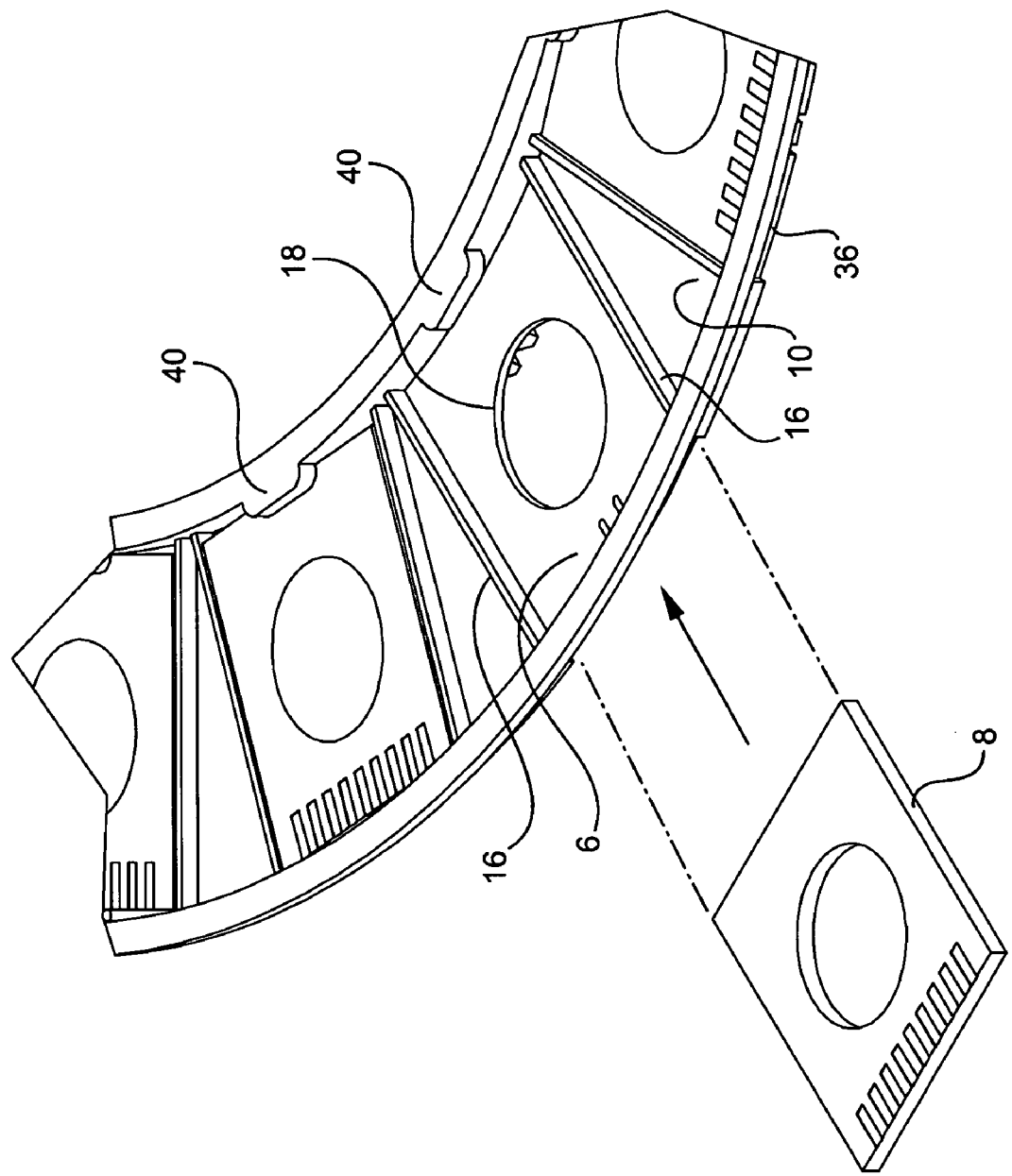
FIG. 5 is a detailed top isometric view of a portion of the slide cartridge shown in FIG. 3, formed in accordance with the present invention.

As shown in FIG. 5, the bottom wall 10 includes partitions or ribs 16 protruding upwardly from the top surface thereof. The ribs 16 are spaced apart from one another periodically about the circumference of the lower ring 4, adjacent ribs defining pairs of ribs. The ribs 16 of each pair are spaced apart from each other slightly greater than the width of a reagent test slide 8 so that one test slide may be held in place in the lower ring between a corresponding pair of ribs 16. The ribs 16 not only hold the test slides received by the cartridge in place in the lower ring 4, but they also define with the sidewalls 12, 14 and bottom wall 10 of the lower ring, and the underside surface of the upper ring 2, individual reaction chambers 6 for each test slide. Accordingly, the slide cartridge of the present invention provides a plurality of reaction chambers 6 which receive reagent test slides 8. Alternatively, the slide cartridge, if formed with no partitions or just slightly raised ribs, would have a single reaction chamber defined primarily by its upper and lower rings 2, 4, which receives a plurality of test slides.

Figure 4:
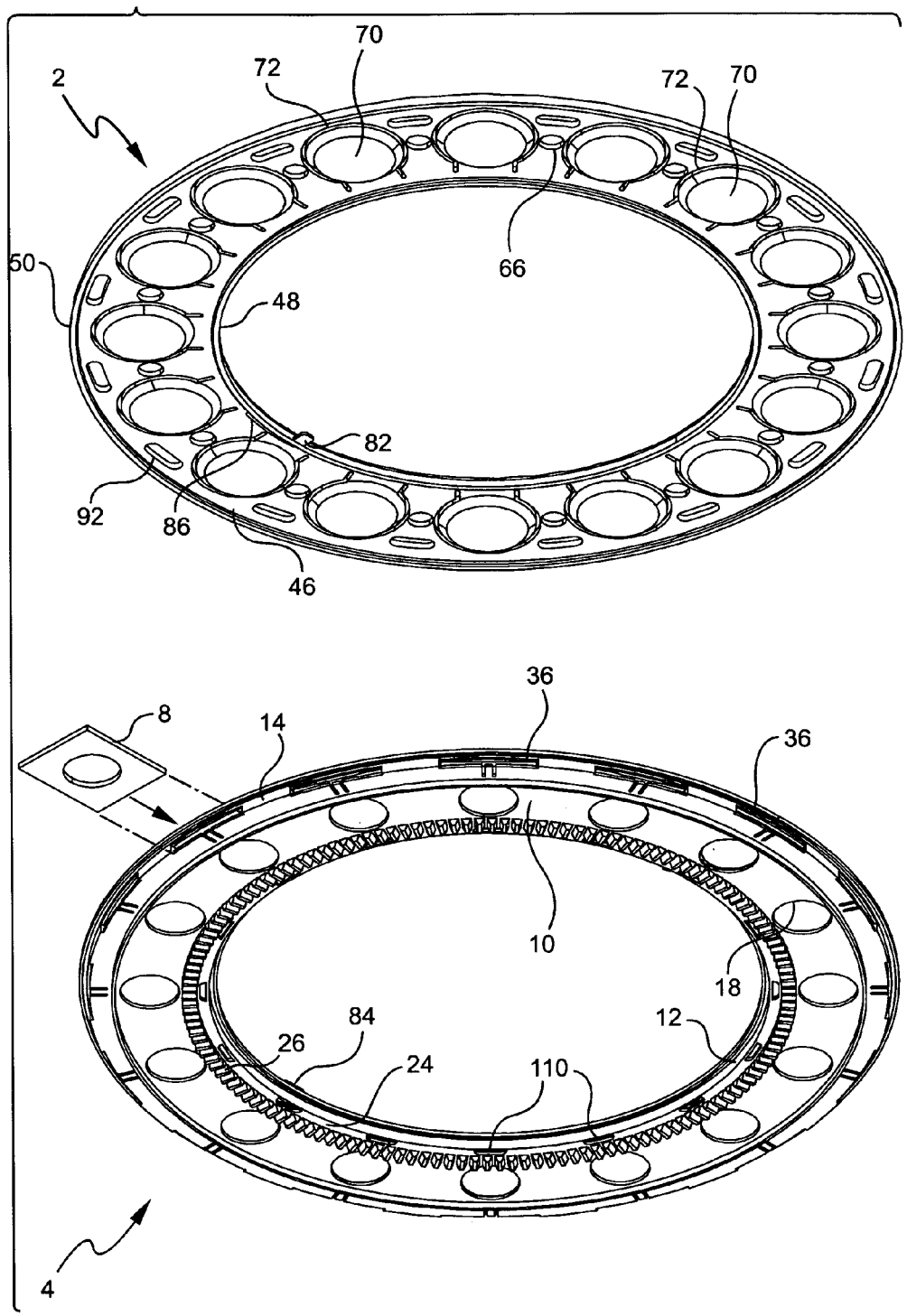
FIG. 4 is a bottom isometric, exploded view of the slide cartridge of the present invention shown in FIGS. 1-3.
Figure 6:
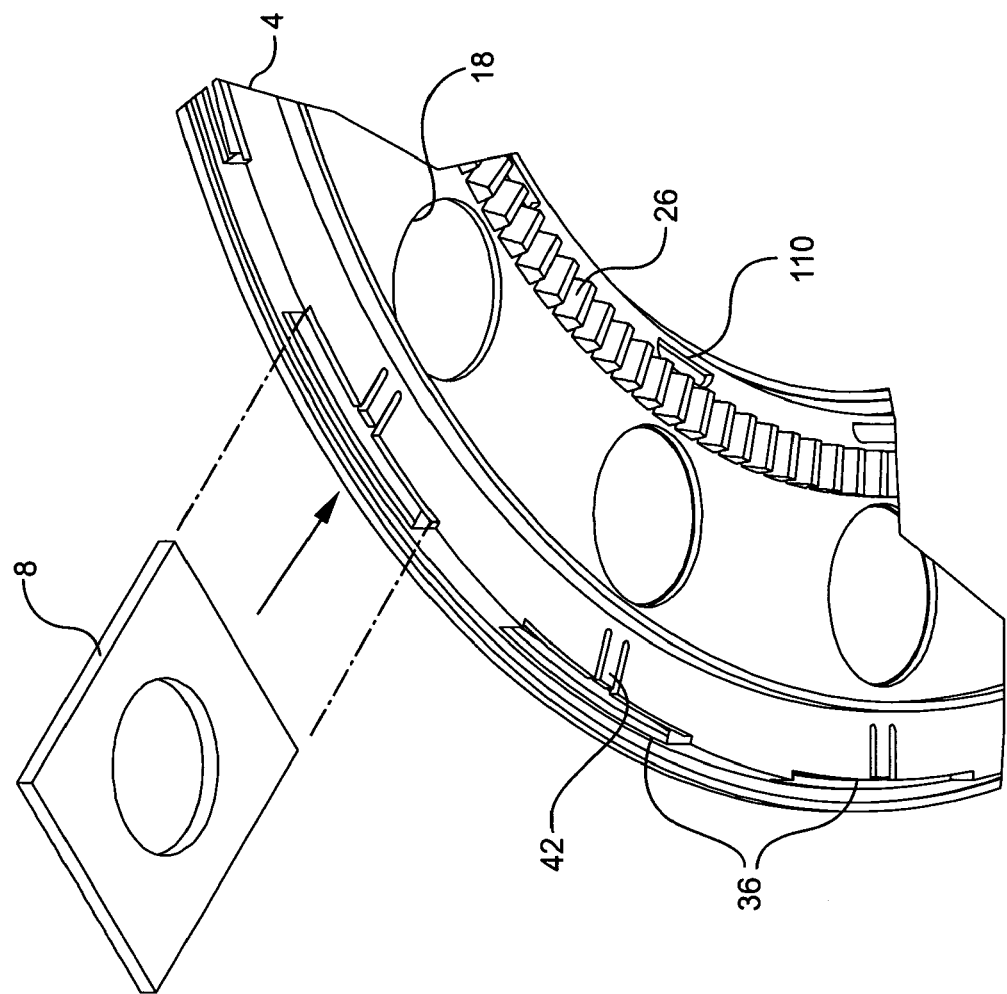
FIG. 6 is a detailed bottom isometric view of a portion of the slide cartridge shown in FIG. 4, formed in accordance with the present invention.

As shown in FIGS. 4 and 6, the bottom wall 10 of the lower ring 4 includes a plurality of openings or viewing windows 18 formed through the thickness thereof and spaced apart circumferentially about the lower ring. The viewing windows 18 are particularly positioned in the bottom wall 10 so as to be in alignment with the exposed underside of the film 20 of the reagent test slides 8 mounted in the slide cartridge. These viewing windows 18 are provided so that the test slides are exposed through the bottom wall 10 of the lower ring to a reflectometer 22 of the chemical analyzer, without the test slides 8 ever having to be removed from their corresponding reaction chambers 6. In other words, colorimetric measurements are performed by the reflectometer 22 while the test slides 8 remain in their respective reaction chambers 6.

The lower ring 4 may further include a hub 24 extending radially outwardly from the inner sidewall 12. On the undersurface of the hub 24 is formed a plurality of gear teeth 26 in a circumferential track, as shown in FIG. 4. The teeth 26 engage a pinion gear 28 mounted to the shaft of a motor, preferably a reversible DC stepping motor 30 (or any other mechanical means of imparting controlled motion), of the chemical analyzer, the rotation of which is controlled by electronic circuitry 32, including a microprocessor or computer 34, and associated software. The motor 30, and associated electronic circuitry 32 and software which control the motor, allow the cartridge, when received by the chemical analyzer, to be rotated therein, the degree of rotation being precisely known and controlled by the analyzer electronics and software.

As shown in FIGS. 4 and 6, the outer sidewall 14 of the lower ring 4 may have formed through the thickness thereof insertion slots 36 for receiving reagent test slides 8 therethrough, the slides being either pre-loaded by the manufacturer of the cartridge or selectively loaded by the operator prior to conducting a test. Each slide insertion slot 36 is aligned and communicates with a corresponding reaction chamber 6. The height of the slots 36 is preferably just slightly greater than the thickness of the frame 38 of the test slide 8 so that the test slide, when mounted in its corresponding reaction chamber 6, at least partially blocks and seals the slide insertion slot 36 so as to render the reaction chamber as a sufficiently closed receiving cavity for the slide, which would minimize evaporation of the sample fluid deposited thereon and maintain the slides at a predetermined temperature during incubation and analysis.

As shown in FIG. 5, the inner sidewall 12 of the lower ring 4 includes a plurality of tabs 40, each of which protrudes radially into a corresponding reaction chamber 6 and above the upper surface of the bottom wall 10 a distance which is slightly greater than the thickness of the test slide 8 received by the reaction chamber. Each tab 40 snugly receives a test slide 8 inserted into the slide cartridge and helps hold the test slide in its proper place.

A plurality of clips 42 is preferably formed resiliently in the bottom wall 10 of the lower ring 4, each clip 42 being positioned in proximity to a corresponding slide insertion slot 36. Each resilient clip 42 has a free end with a barb 44 protruding into the reaction chamber 6. When a test slide is fully inserted in the slide cartridge, one edge of the slide is received under a corresponding tab 40 of the lower ring, and the opposite edge of the slide is engaged by the barb 44 of the resilient clip 42. Thus, the ribs 16 on the lateral sides of the test slides, the tabs 40 and the resilient clips 42 cooperate to hold the test slides 8 in their proper positions in the slide cartridge and reduce or prevent their movement relative to the cartridge. The resilient clips 42 further insure that the test slides 8 will not inadvertently slip back through the slide insertion slots 36 as the slide cartridge is rotated in the chemical analyzer.

The upper ring 2 of the slide cartridge includes a primary or top wall 46, and inner and outer sidewalls 48, 50 (see FIG. 11) which are radially spaced apart from one another and which extend perpendicularly to the top wall 46 from opposite edges of the top wall. The upper ring 2 is press fitted onto the lower ring 4 so that the two rings are securely held together but are at least partially rotatable with respect to each other. The preferred structure which holds the upper and lower rings 2, 4 together and which allows them to rotate relative to each other will now be described.

Figure 11:
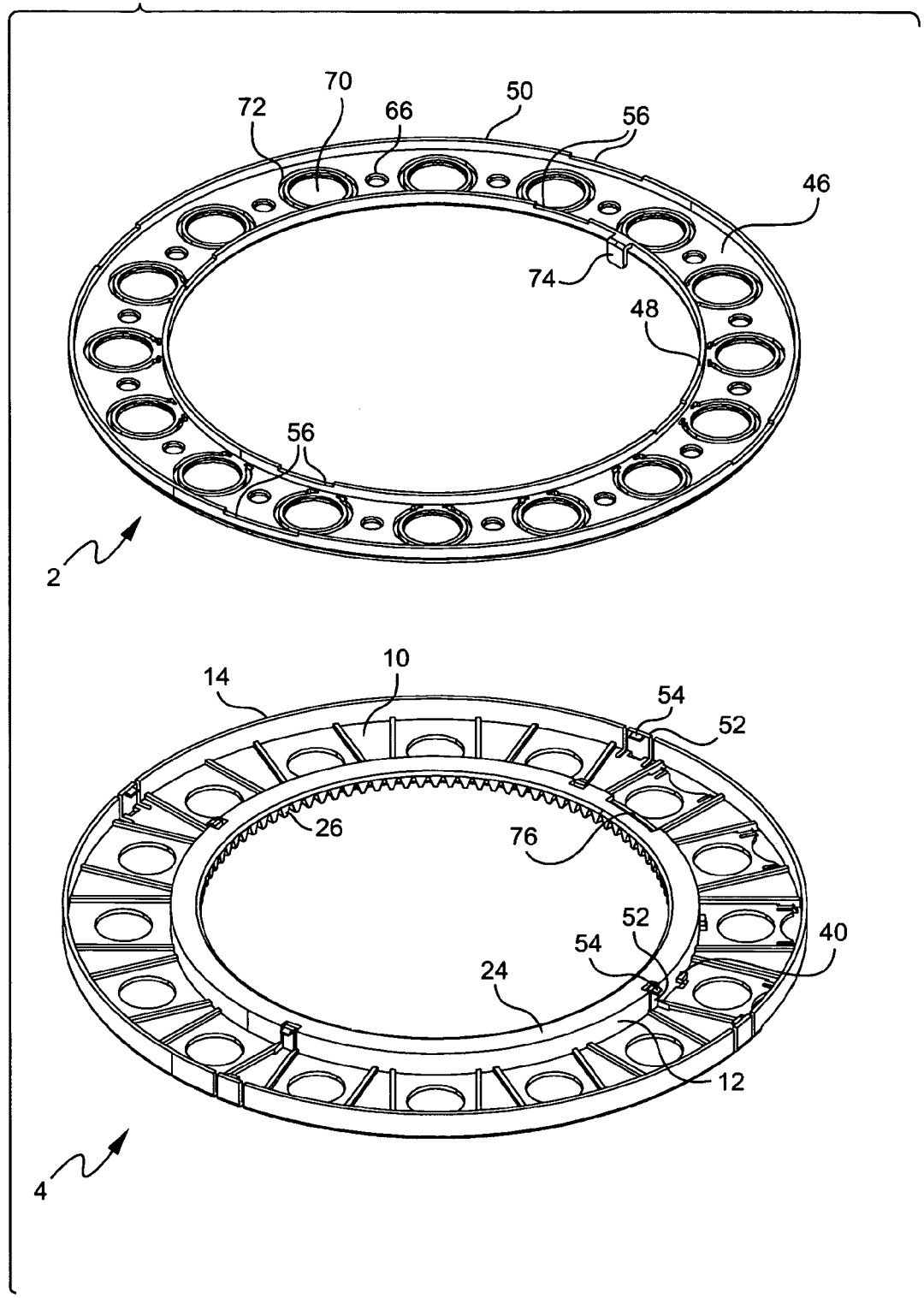
FIG. 11 is a top isometric, exploded view of the slide cartridge shown in FIGS. 9 and 10, formed in accordance with the present invention.
Figure 12:
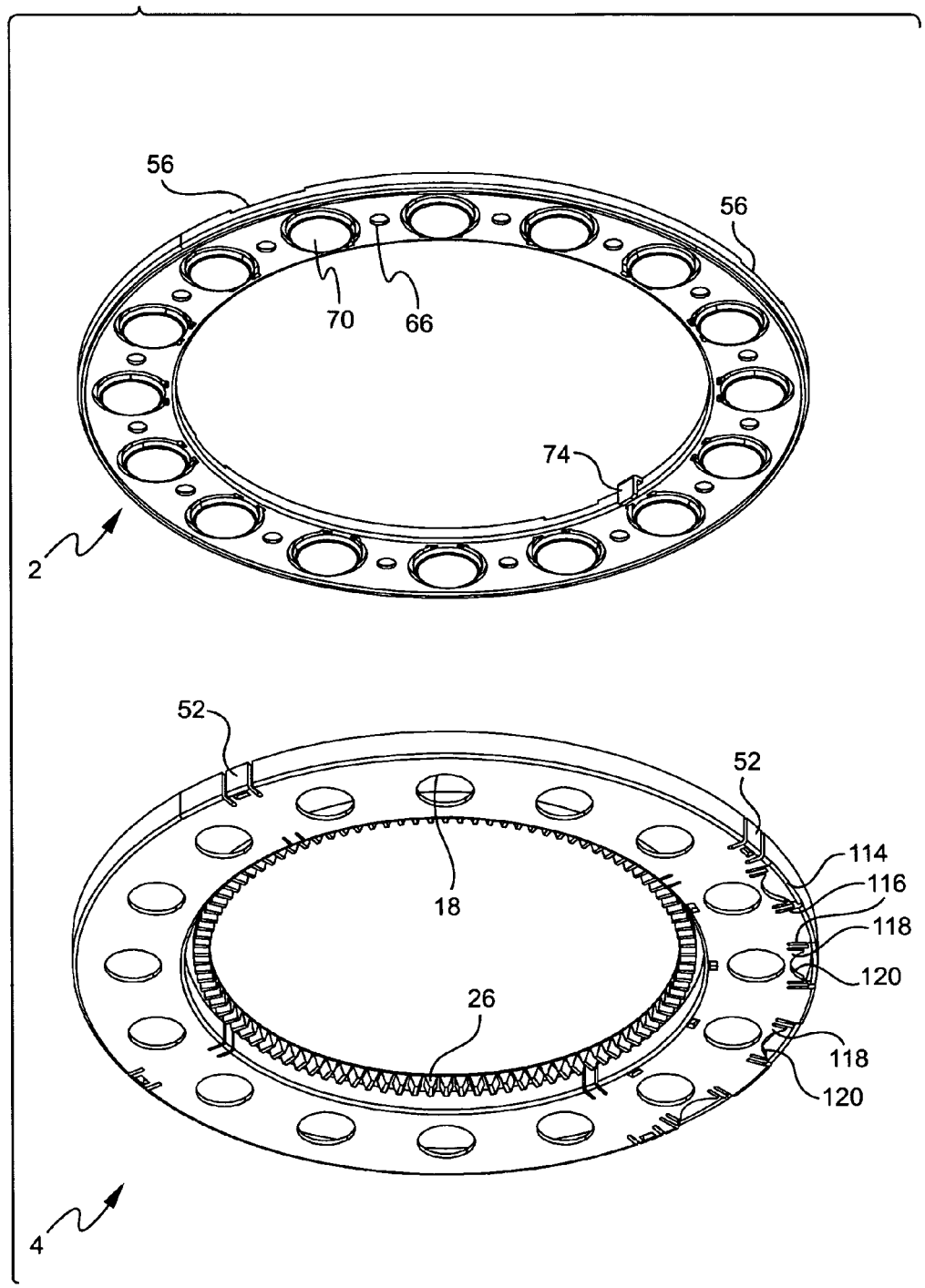
FIG. 12 is a bottom isometric, exploded view of the slide cartridge shown in FIGS. 9 and 10, formed in accordance with the present invention.

Referring now to FIG. 11, it will be seen that the inner and outer sidewalls 12, 14 of the lower ring 4 include periodically circumferentially spaced, resilient clips 52 having free standing ends. The free standing end of each resilient clip includes a barb 54 formed on one surface thereof. The clips 52 of the inner sidewall 12 are radially aligned with corresponding clips 52 on the outer sidewall 14, with their barbs 52 facing one another. The clips 52 are provided to hold the upper ring 2 in place on the bottom ring 4, but allow at least partial rotation thereof with respect to the bottom ring 4.

Notches 56 are cut into the upper edge of each of the inner and outer sidewalls 48, 50 of the upper ring 2 and spaced apart periodically about the periphery of each of the sidewalls, with the same circumferential spacing as that of the resilient clips 52 of the inner and outer sidewalls 12, 14 of the lower ring 4, respectively. The notched-out portions 56 of the inner and outer sidewalls 48, 50 of the upper ring 2 define an arc sufficient to allow the upper ring 2 to rotate at least a predetermined distance with respect to the lower ring 4 when the two rings are mated together. The outer radial width of the upper ring 2, that is, including its inner and outer sidewalls 48, 50, is slightly less than the inner width of the lower ring 4, that is, between its inner and outer sidewalls 12, 14, so that the upper ring 2, including its sidewalls, may be received by the lower ring 4 between its sidewalls. When the two rings are press fitted together, the barbs 54 on the resilient clips 52 formed in the inner and outer sidewalls 12, 14 of the lower ring engage the recessed edges of the inner and outer sidewalls 48, 50 of the upper ring at the bottom of the notches 56 and hold the upper ring 2 in place within the confines of the lower ring 4. As stated previously, the width of the upper ring 2, measured radially, is slightly less than the radial distance between the upper and lower sidewalls 12, 14 of the lower ring 4 to allow the upper ring 2 to rest within the confines of the lower ring, between the inner and outer sidewalls 12, 14 of the lower ring 4. However, the barbs 54 of the resilient clips 52 loosely engage the recessed edges of the upper ring sidewalls at the notches 56 to allow the upper and lower rings 2, 4 to at least partially rotate with respect to each other. The arcuate length of the notches 56 formed in the sidewalls of the upper ring 2 is such as to ensure the full extent of the required relative movement of the rings, in order to permit the uncovering, sample spotting and re-covering of the test slides 8, as will be described in greater detail.

Figure 7A:
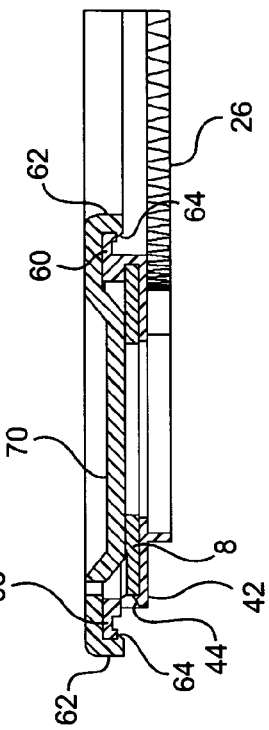
FIG. 7A is a cross-sectional view of the slide cartridge shown in FIG. 7, taken along line 7A-7A of FIG. 7.

Alternatively, the slide cartridge of the present invention may have the structure shown in the cross-sectional view of FIG. 7A which allows the upper and lower rings 2, 4 to be snap fitted together. More specifically, the lower ring 4 may include first and second flanges 58, 60 respectively extending radially outwardly in opposite directions from the outer and inner sidewalls 14, 12 of the lower ring. The upper ring 2 is formed with resilient hooked ends 62 extending radially in opposite directions from the primary or top wall 46 of the upper ring, each hooked end 62 further extending downwardly therefrom and including a barb or protrusion 64 at its free end. The upper and lower rings 2, 4 are snap fitted together by pressing the resilient hooked ends 62 of the upper ring onto the first and second flanges 58, 60 of the lower ring, so that the barbs or protrusions 64 on the hooked ends 62 engage the underside of the first and second flanges 58, 60 to hold the upper and lower rings together. The hooked ends 62 of the upper ring 2 and the first and second flanges 58, 60 of the lower ring 4 are dimensioned to ensure that the upper and lower rings will remain mated together but also to allow sufficient play between the two so that the upper and lower rings may at least partially rotate relative to one another. It is envisioned, of course, that the placement of the hooked ends 62 and the first and second flanges 58, 60 on the upper and lower rings may be exchanged, with the hooked ends 62 residing on the lower ring 4 and the first and second flanges 58, 60 residing on the upper ring 2, to provide the same snap fit, rotatable mating of the upper and lower rings. It is further envisioned that only one hooked end 62 and only one of the first and second flanges 58, 60 may be provided in order to rotatably secure the upper ring 2 to the lower ring 4.

Figure 3:
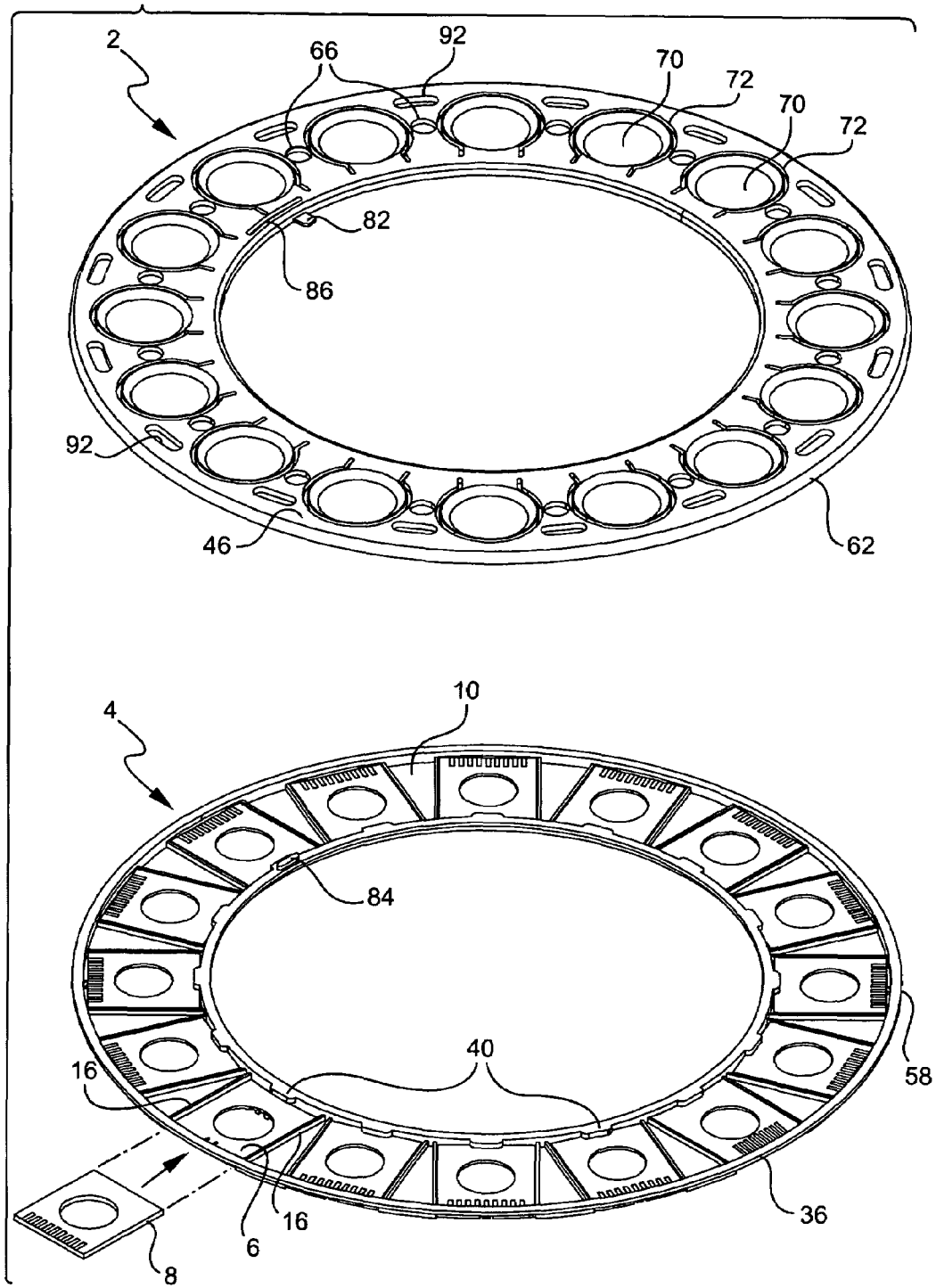
FIG. 3 is a top isometric, exploded view of the slide cartridge shown in FIGS. 1 and 2, formed in accordance with the present invention, and illustrating the insertion and mounting of reagent test slides therein.
Figure 8:
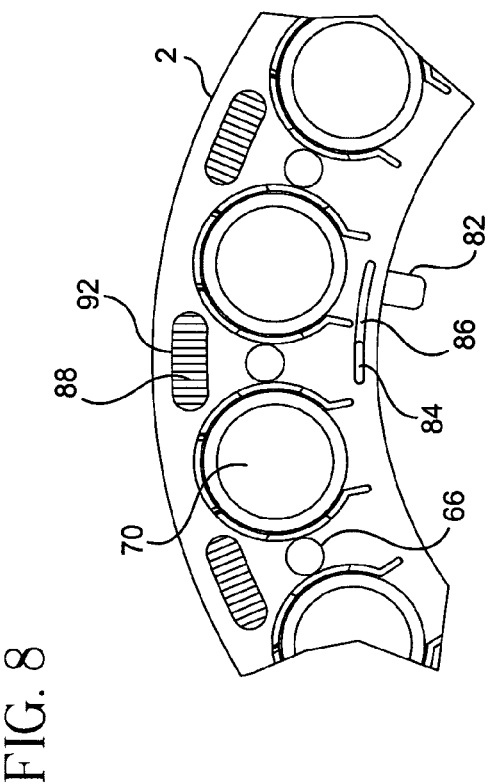
FIG. 8 is a top plan view of a portion of the slide cartridge shown in FIG. 3, formed in accordance with the present invention, and illustrating a second relative position of components of the slide cartridge.
Figure 7:
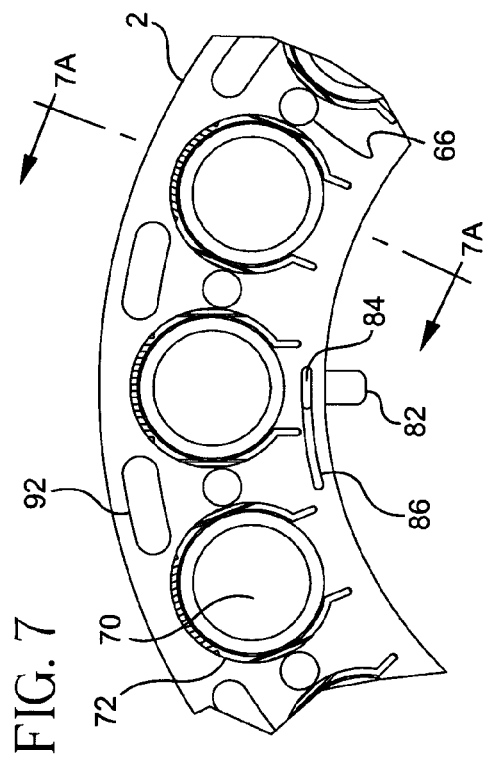
FIG. 7 is a top plan view of a portion of the slide cartridge shown in FIG. 3, formed in accordance with the present invention, and illustrating a first relative position of components of the slide cartridge.
Figure 9:
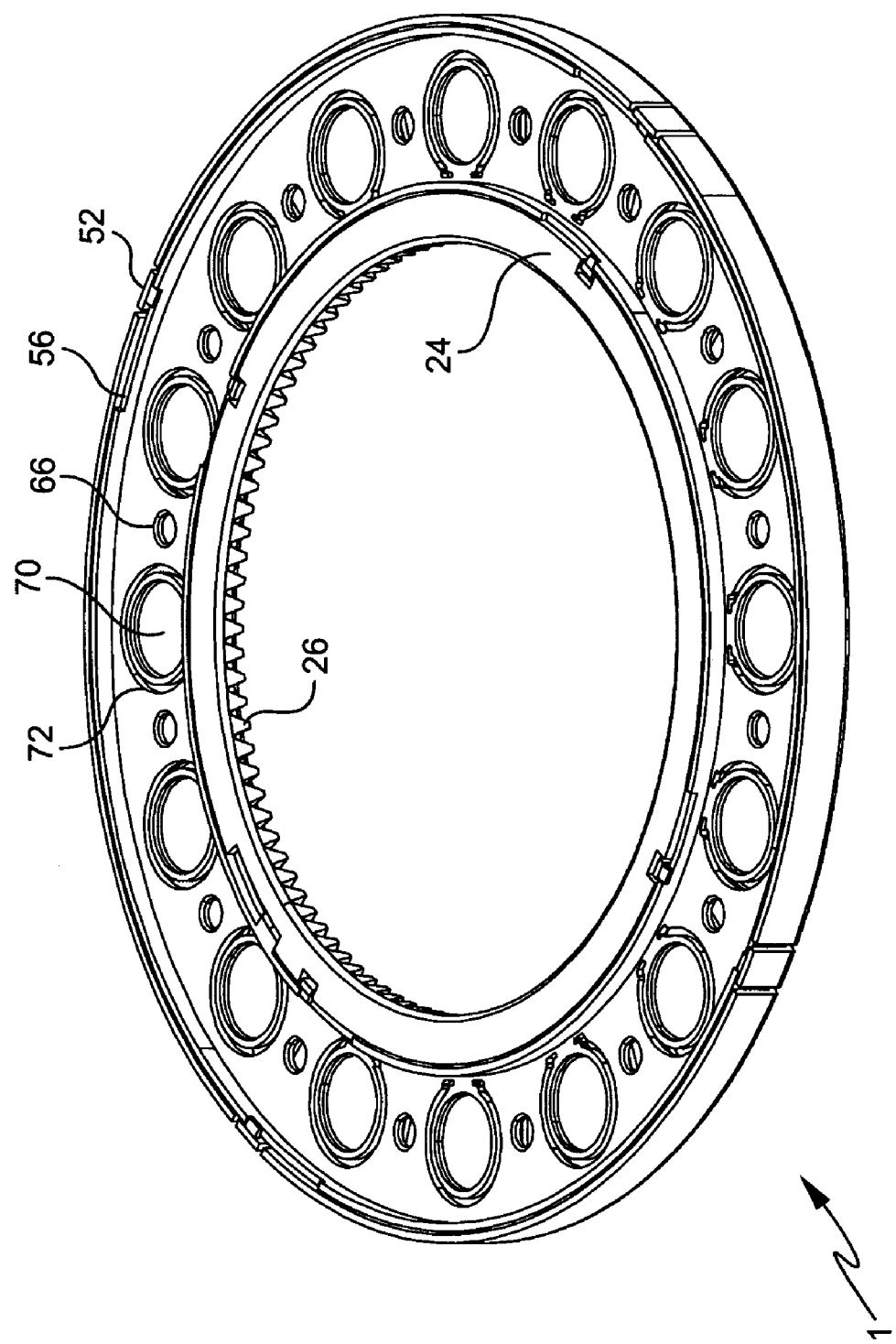
FIG. 9 is a bottom isometric view of a second embodiment of a slide cartridge formed in accordance with the present invention.
Figure 10:
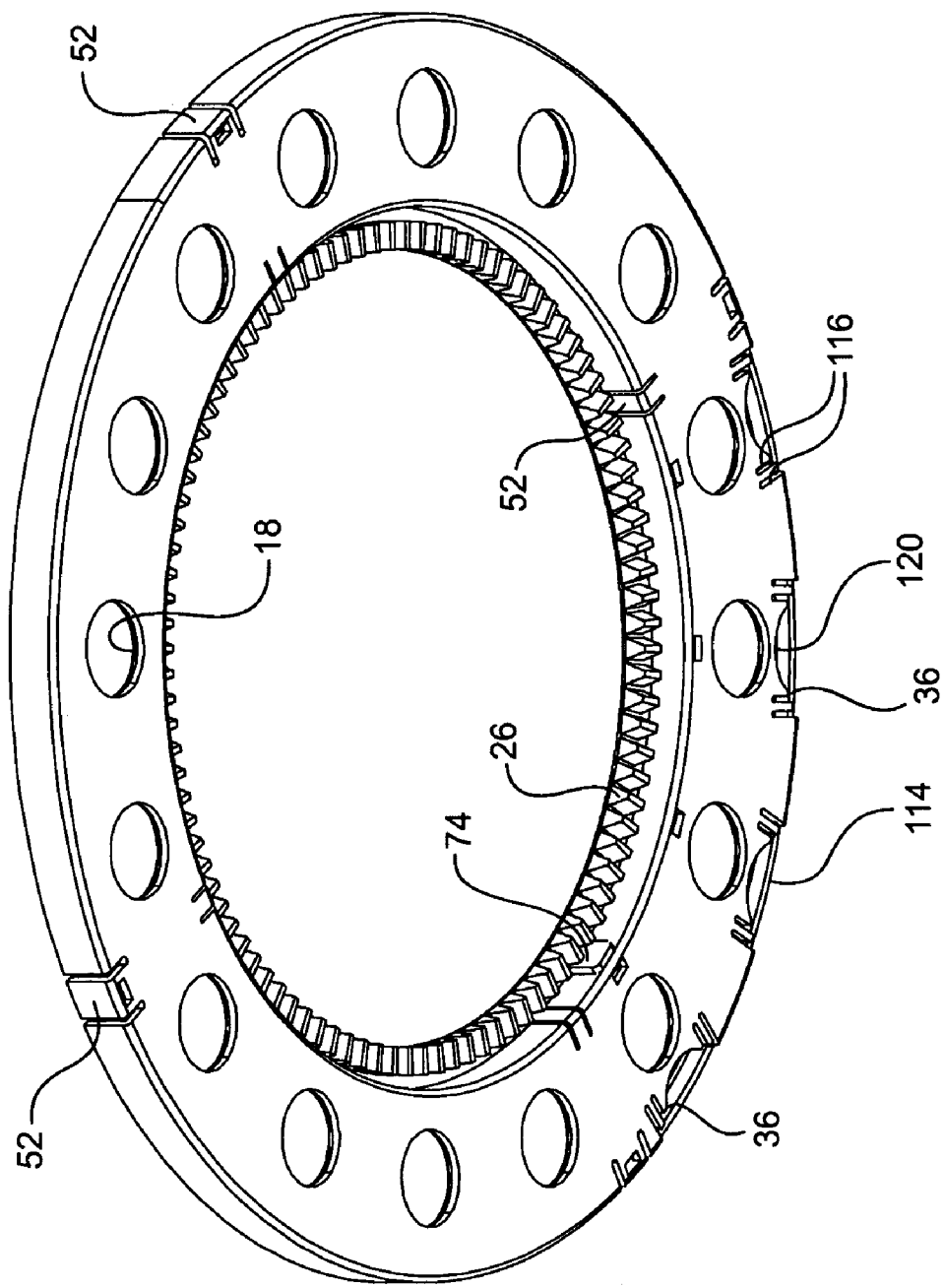
FIG. 10 is a top isometric view of the second embodiment of the slide cartridge shown in FIG. 9, formed in accordance with the present invention.

As shown in FIGS. 3, 7 and 8, spotter ports 66 are formed through the thickness of the top wall 46 of the upper ring 2. The spotter ports 66 are spaced apart circumferentially, centrally in the radial width of the ring, at predetermined locations about the upper ring 2. The spotter ports 66 are provided for allowing a metering device 68 of the chemical analyzer to deposit a predetermined amount of sample fluid through each spotter port 66 onto the upper side of the film 20 of each test slide 8 containing the dry analyte.

Reaction chamber caps 70 are also formed in the top wall 46 of the upper ring 2, which reaction chamber caps 70 are also spaced apart from each other a predetermined distance circumferentially about the top wall, each reaction chamber cap 70 alternating in sequence with a spotter port 66. The reaction chamber caps 70 closely reside in openings 72 formed through the thickness of the top wall 46 of the upper ring. They are resiliently hinged to the top wall at the wall edge that defines the openings 72, and disposed thereto such that they extend below the underside of the top wall 46 to resiliently and selectively engage the test slides 8 and cover the analyte film side thereof when the test slides are mounted in the slide cartridge of the present invention. The upper ring 2 may be rotated at least partially on the lower ring 4 so as to allow the reaction chamber caps 70 to selectively cover and uncover the test slides 8. The reaction chamber caps 70 are provided to minimize evaporation of the fluid sample deposited on the test slides 8.

As shown in FIG. 11, a rotation control arm 74, or lever, is fixedly attached to the upper ring 2 and extends through an arcuate slot 76 formed through the thickness of the lower ring 4. An arm 78 attached to a solenoid 80 or to a shaft of a motor controlled by the chemical analyzer selectively engages the control arm 74 of the upper ring 2 to cause the upper ring to rotate through a predetermined arc with respect to the lower ring 4. The upper ring 2 is preferably rotated between a first position, where the spotter ports 66 are aligned with and situated directly over the analyte film 20 of corresponding test slides 8 mounted in the lower ring 4, and a second position, where the reaction chamber caps 70 are aligned with and cover the analyte film 20 of each test slide. The arcuate length of the slot 76 defines the extent of relative movement of the upper and lower rings 2, 4.

Alternatively, and as shown in FIG. 3, the rotation control arm may be a tab 82 that is affixed to the inner sidewall 12 of the upper ring 2 and extends radially outwardly therefrom. The lower ring 4 includes a protrusion 84 extending upwardly from the top surface of the inner sidewall 12 of the lower ring. The protrusion 84 is received by an arcuate slot 86 formed through the thickness of top wall 46 of the upper ring 2. The rotation control arm 74 (i.e., the tab 82 in this embodiment) is similarly selectively engaged by an arm 78 attached to a solenoid 80 or to a shaft of a motor controlled by the chemical analyzer to cause the upper ring 2 to rotate through a predetermined arc with respect to the lower ring 4. In other words, in this and the previously described embodiment, the solenoid arm 78 may engage the rotation control arm 74 to prevent movement of the upper ring 2 while the motor 30 rotates the lower ring. Alternatively, the arm 78, if attached to a motor, may exert a force on the rotation control arm 74 in either opposite direction to rotate the upper ring 2 on the lower ring 4, while the motor 30 and its pinion gear 28 engaging the gear teeth 26 on the lower ring 4 prevent the lower ring from rotating. The protrusion 84 moves through the slot 86 when the upper and lower rings rotate relative to each other until it engages either opposite end of the slot. Thus, the arcuate length of the slot 86 defines the extent of relative movement of the upper and lower rings 2, 4.

Figure 15:
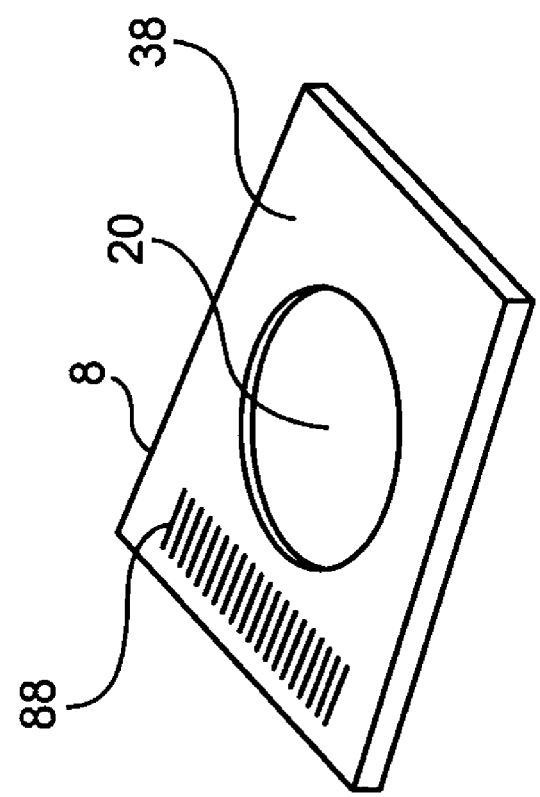
FIG. 15 is a top isometric view of a reagent test slide formed in accordance with the present invention, for use with the slide cartridge and chemical analyzer of the present invention.

The test slides 8 which may be used in the slide cartridge and chemical analyzer of the present invention may have a frame 38 which is rectangular in shape, such as those shown in the aforementioned Sekine et al. patent or in the '229 Heidt et al. patent. As such, adjacent ribs 16 of the rib pairs are disposed parallel to each other and spaced apart from each other a distance which is slightly greater than the width of a test slide 8 so that a test slide may be received closely between the ribs 16. Alternatively, and in accordance with the present invention, the test slides 8 may be trapezoidal in shape, as shown in FIG. 15. As such, each pair of ribs 16 which receive between them a test slide 8 may be radially disposed on the upper surface of the bottom wall 10 of the lower ring 4 and spaced apart, again, slightly more than the width of the test slide. The ribs 16 help guide the test slides into proper placement in the lower ring 4 as they are being either inserted through the slide insertion slots 36 formed in the outer sidewall of the lower ring, after the upper and lower rings have been assembled, or placed directly onto the bottom wall 10 of the lower ring 4 while the lower ring is open and accessible and prior to its assembly with the upper ring 2. The ribs 16 maintain the position of each test slide 8 in the cartridge within a corresponding reaction chamber 6 and ensure that the test slides will be in proper position over the viewing windows 18 formed in the bottom wall 10 of the lower ring.

An advantage of having reagent test slides 8 which are trapezoidal in shape is that this shape allows a greater number of test slides to be mounted on the lower ring 4 of a given radius, or stated another way, allows a smaller radius lower ring 4 to be used for a given number of test slides 8, compared to the situation where conventional rectangular test slides are used. Furthermore, the trapezoidal shape of the reagent test slides 8 ensures that the test slides will be properly oriented when they are inserted in the slide cartridge. The ribs 16 of each rib pair partially define the trapezoidal outline of the test slides and will not accept between them a test slide if it is inserted through the slide insertion slot 36 backwards or sidewise.

Also, each test slide 8 preferably includes information 88, imprinted on one side of the frame 38 and preferably situated along the larger (i.e., base) side of the slide frame. The information can include, for example, slide type, manufacturing date, expiration date, lot number and/or calibration information. The information can be in any suitable readable form, such as bar code or universal product code (UPC). The information 88 also helps a user orient the test slides properly during insertion into the slide cartridge to prevent the slides from being inserted upside down.

The information 88 is read by an information reader 90, such as an optical code reader, preferably mounted in the chemical analyzer above the slide cartridge placed therein. Clear or transparent windows 92 formed of plastic, glass or the like are mounted in openings formed through the upper ring 2. Each window 92 is positioned in overlying relationship with that portion of a corresponding test slide 8 on which the information 88 is imprinted. If desired, the windows 92 may be positioned in alignment with the spotter ports 66, as shown in FIG. 3, and the upper ring 2 may be rotated with respect to the lower ring 4 so that the windows 92 selectively overlie the information 88 imprinted on each slide. As the slide cartridge is rotated within the chemical analyzer, the information 88 is read through each window 92 by the information reader 90 as it passes under the information reader, and signals generated thereby are provided to the electronic circuitry 32 and its associated software for use during the analysis stage. A microprocessor or computer 34, forming part of the chemical analyzer, senses these signals and interprets the information, and determines what tests are to be performed. Alternatively, either the upper and lower ring 2, 4, or both, may be made partially or entirely from a clear or transparent material so that the information 88 may be read by the information reader 90 through either the upper or lower ring.

The slide cartridge of the present invention may come with a plurality of pre-loaded test slides 8. Common test slides used in biological fluid analysis include one for a calcium (Ca) test, another for an ammonia (NH$_3$) test, and a third for a glucose (Glu) test. The test slides 8 may be mounted in the lower ring 4 of the slide cartridge prior to snap-fitting the upper ring thereon, or may be pre-loaded through the slide insertion slots 36 formed in the outer sidewall 14 of the lower ring 4 after the upper and lower rings have been assembled together. Alternatively, test slides 8 may be inserted by the user in available (i.e., empty) reaction chambers 6 by inserting the test slides through the slide insertion slots 36 formed in the outer sidewall 14 of the lower ring 4. For slide cartridges with pre-loaded test slides, the upper ring 2 is rotated on the lower ring such that the reaction chamber caps 70 cover the analyte coated film 20 of each test slide 8, and the entire slide cartridge can be packaged to prevent deterioration of the analyte on the slides and to prolong the shelf life of the preloaded test slides. Moisture impervious packaging with or without desiccant or vacuum sealing is preferred.

The user would remove the slide cartridge from the package, insert any additional slides into the slide cartridge as desired, and place the slide cartridge into the chemical analyzer.

Figure 13:
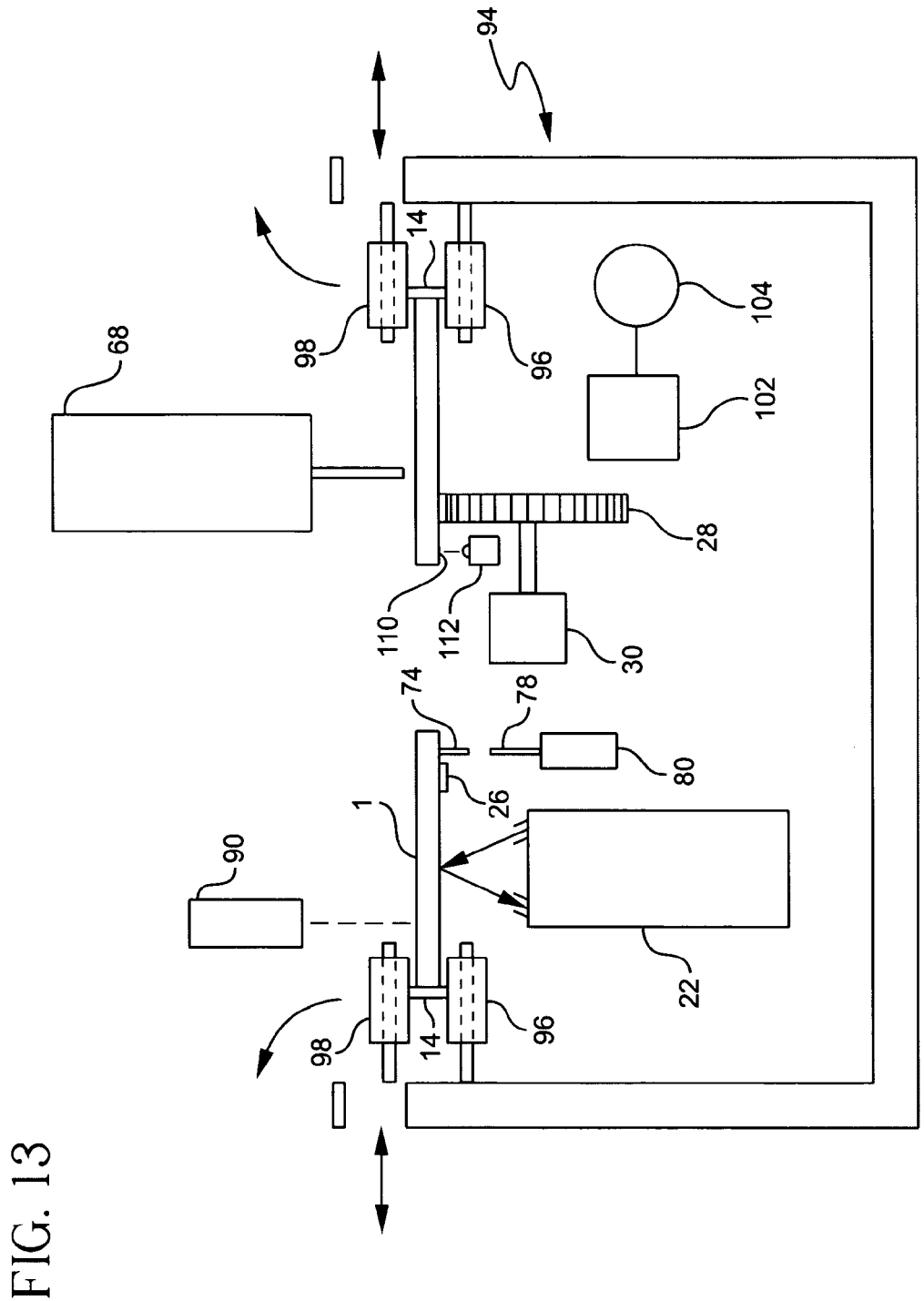
FIG. 13 is a pictorial, cross-sectional illustration of a chemical analyzer formed in accordance with the present invention, illustrating its cooperation with the slide cartridge of the present invention.

As illustrated by FIG. 13, the chemical analyzer 94 supports the slide cartridge 1 in engagement with a pinion gear 28 mounted on a shaft of a motor, which is preferably a reversible DC stepping motor 30, which is controllably driven by an electronic circuit 32 and software of the chemical analyzer. Controlled rotation of the slide cartridge by the motor 30 permits the chemical analyzer to precisely locate each test slide 8 relative to the other stations (e.g., the metering device 68 and the reflectometer 22) of the analyzer. The motor pinion gear 28 will engage the toothed gear track 26 formed on the hub 24 of the lower ring, and rotate the slide cartridge to sequentially position each test slide 8 under the sample metering device 68 and above the reflectometer 22 of the chemical analyzer during its operation. Alternatively, any combination of rotational drive/control that can interact with the cartridge is contemplated herein, provided sufficient control of cartridge orientation is achieved.

It is envisioned that the chemical analyzer 94 may support the slide cartridge 1 in engagement with the pinion gear 28 of the motor in various ways. One way, for example, is to have a plurality of spaced apart, freely rotating, lower rollers 96, which allow the lower edge of the outer sidewall 14 of the lower ring to rest thereon. The rollers 96 are positioned relative to the pinion gear 28 such that the gear track 26 of the slide cartridge engages the pinion gear 28 of the motor. To prevent the gear track 26 of the slide cartridge from disengaging from the pinion gear 28 of the motor, a plurality of spaced apart, freely rotating, upper rollers 98, which either pivot or move axially into position, engage the upper edge of the outer sidewall of either the upper ring 2 or the lower ring 4 so that the slide cartridge is sandwiched between the upper and lower rollers 98, 96 of the chemical analyzer and can rotate freely therebetween.

The upper ring 2 may be rotated at least partially with respect to the lower ring 4 by having an arm 78 attached to the solenoid 80 or shaft of a motor selectively engage the rotation control arm 74 of the upper ring. The arm 78 may either move the rotation control arm 74 to rotate the upper ring 2 with respect to the lower ring 4, or it may simply engage the rotation control arm 74, and the stepping motor 30 may drive the lower ring 4 to rotate the lower ring with respect to the upper ring.

The upper ring 2 is rotated with respect to the lower ring 4 such that the spotter ports 66 are aligned with the analyte coated films 20 of the test slides. The motor 30 then rotates the slide cartridge so that each spotter port 66 is sequentially aligned with the sample metering device 68 of the chemical analyzer. The metering device 68 deposits a predetermined amount of fluid sample to be tested onto each test slide 8 through the spotter ports 66. After each test slide is spotted, the rotation control arm 74 is again engaged by the solenoid or motor arm 78 to rotate the upper ring 2 in the opposite direction to allow the reaction chamber caps 70 to again cover the analyte film 20 of each test slide to prevent evaporation of the deposited sample fluid.

The test slides are maintained at a predetermined temperature, which is preferably about 37° C., prior to and during the sample fluid deposition and reflectance measurement steps. For this purpose, the chemical analyzer may include an incubation chamber 100, having a heat source 102 and a temperature sensor 104, such as a thermocouple, in which the entire slide cartridge 1 may be rotated in place in order to maintain the test slides 8 at the desired temperature. Alternatively, the slide cartridge 1 may be made from a material, such as metal, which is thermally conductive and which may be heated to, and maintained at, a predetermined temperature from a heat source 102 that provides heat to the slide cartridge either radiantly, convectionally or conductively.

The slide cartridge is intermittently rotated above the reflectometer 22 of the chemical analyzer which measures the calorimetric changes in the film 20 of each test slide by reflecting light of predetermined wavelengths off the test slide film through the viewing windows 18 formed in the lower ring 4.

Figure 14:
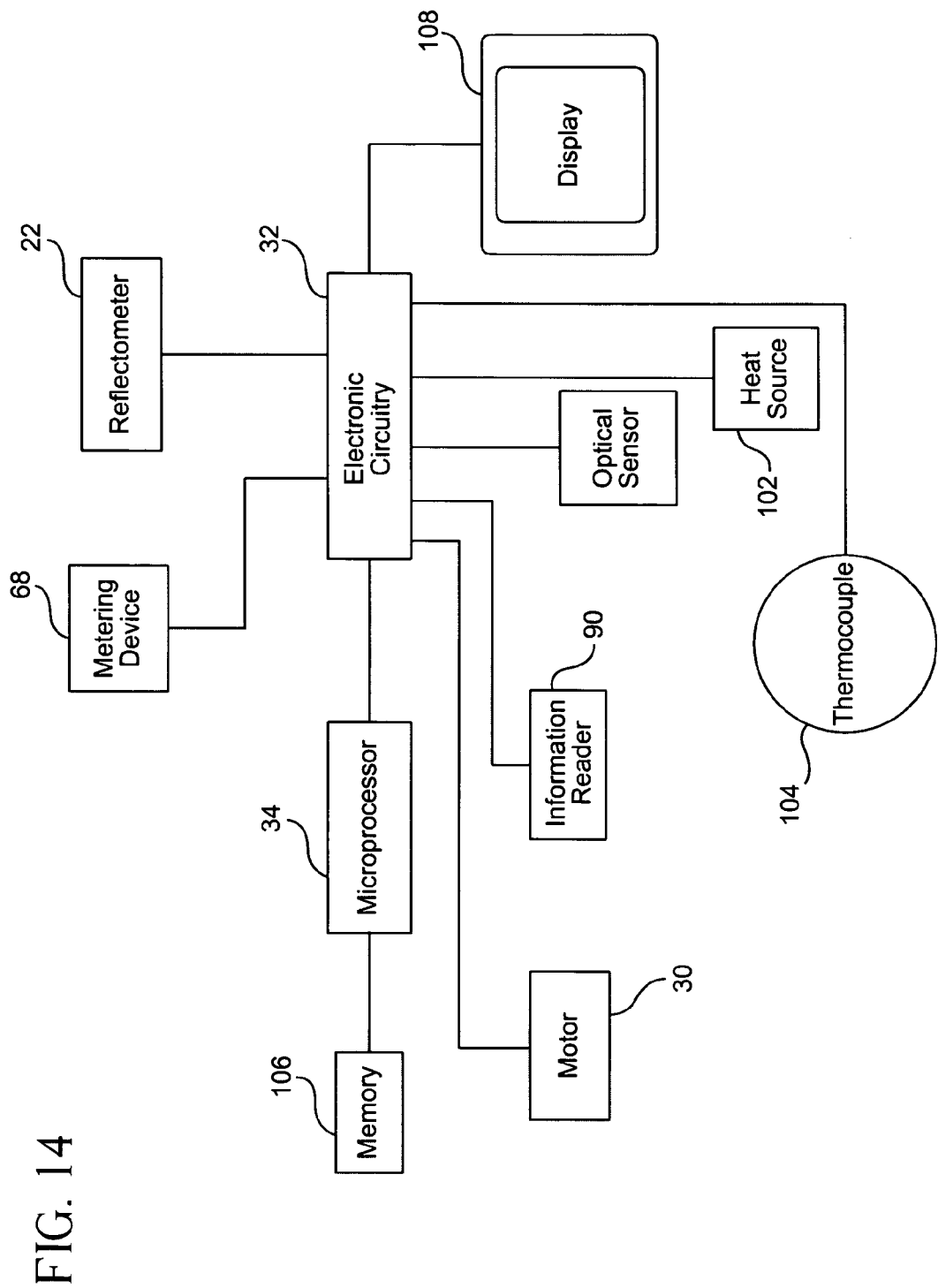
FIG. 14 is a block diagram of the circuit and various components of the chemical analyzer formed in accordance with the present invention.

As shown in FIG. 14, the chemical analyzer also includes electronic circuitry 32 connected to the sample metering device 68, motor 30, optical sensors 90, 112, solenoid 80 and reflectometer 22, a computer or microprocessor 34 having an associated memory 106 for storing software and measurement data and for operating the chemical analyzer and analyzing the measurements taken by the reflectometer 22, and a display 108 for displaying to the user the results performed by the analyzer on the sample fluid tested. The operation and structure of each of these components, and the electronic circuitry and software, can be similar to those disclosed in the aforementioned U.S. Pat. No. 5,089,229, the disclosure of which is incorporated herein by reference.

After the chemical analysis of the sample has been completed, the slide cartridge 1 of the present invention containing the used test slides 8 is removed from the chemical analyzer and properly disposed of, without the necessity of removing the test slides therefrom.

The underside of the hub 24 may further include a series of notches or protrusions 110 formed in the surface thereof which act as registration codes. Each set of notches or protrusions 110 is situated radially in alignment with a corresponding reaction chamber 6, or a viewing window 18 formed in the lower ring 4, and is detected by an optical reader or sensor 112 of the chemical analyzer, which is situated below the lower ring 4 and in alignment with the notches or protrusions 110 as the slide cartridge is rotated. The registration codes defined by the notches or protrusions 110 allow the chemical analyzer to register the position of each test slide 8 in the slide cartridge so that the measurements taken by the reflectometer 22 may be properly correlated to the corresponding test slides 8.

FIGS. 9 through 12 illustrate another embodiment of the slide cartridge formed in accordance with the present invention. For the components of the slide cartridge shown in FIGS. 9-12 which are similar in structure and function to those components shown in FIGS. 1-8, like reference numbers are used, and the structure of those components have been previously described and will not be further described with respect to the embodiments shown in FIGS. 9-12.

As shown in FIGS. 9-12, the outer sidewall 14 of the lower ring 2 need not have the same structure that defines the slide insertion openings described previously and shown in FIG. 6. Rather, the outer sidewall 14 of the lower ring may be substantially whole, and the slide insertion slots 36 may be formed at the lower edge of the outer sidewall 14 where it meets the bottom wall 10 of the lower ring.

More specifically, in this form of the slide cartridge of the present invention, a number of reagent test slides 8 are pre-loaded onto the lower ring 4 prior to the upper ring 2 being press fitted thereon to form the assembled slide cartridge. However, one or more reaction chambers 6 may be left empty for the user to insert test slides into the cartridge. In the slide cartridge illustrated in FIGS. 9-12, for example, there are four reaction chambers 6 which are left empty for this purpose, and the remaining reaction chambers are pre-loaded with reagent test slides 8. Accordingly, for reaction chambers which carry pre-loaded reagent test slides, no slide insertion slots need be formed in the outer sidewall 14 of the lower ring. This is true for either the embodiment of the slide cartridge shown in FIGS. 1-8, or the embodiment shown in FIGS. 9-12.

FIGS. 9-12 illustrate an alternative structure for forming the slide insertion slots 36 in the slide cartridge of the present invention. In this particular form, the outer sidewall 14 may be slightly shortened at its lower edge over portions about its periphery which align with, and correspond to, the empty reaction chambers 6 to allow the user to insert user-selectable reagent test slides in such reaction chambers. The shortened lower edge 114 of the outer sidewall of the lower ring over such portions do not engage the bottom wall 10 of the lower ring 4, thereby defining a space therebetween. Additionally, the bottom wall 10 includes slots or cuts 116 formed through its thickness which extend generally radially, with respect to the lower ring, or parallelly, with respect to each other, partially across the width of the bottom wall 10, the cuts 116 being situated in proximity to the lateral sides of the reaction chambers 6, for example, close to the ribs 16 formed on the upper surface of the lower ring. Adjacent cuts 116 formed in the bottom wall define therebetween resilient, hinged portions 118 of the major portion of the bottom wall 10 which may be deflected downwardly to allow the user to insert a selected test slide between the shortened portion 114 of the outer sidewall 14 and the hinged portion 118 of the bottom wall immediately below the sidewall shortened portion. Thus, the sidewall shortened portion 114 and the hinged bottom wall portion 118 situated directly below it define therebetween a slide insertion slot 36 for the purpose of allowing the user to load a selected test slide into a particular empty reaction chamber 6 situated in alignment with the thus-defined slide insertion slot 36.

To further facilitate the insertion of reagent test slides into the slide insertion slots 36, the unattached or free end of the hinged bottom wall portion 118 may be recessed to define a cutout 120, which is preferably concave, which cutout 120 provides further depth to the slide insertion slot to facilitate the insertion of a reagent test slide 8 therethrough and into a corresponding reaction chamber 6.

The slide cartridge 1 of the present invention facilitates the operation of a chemical analyzer. By having preloaded slides 8, the slide cartridge may be easily placed in the chemical analyzer without the operator having to handle individual test slides and possibly improperly touching the slide films 20. No test slide injector mechanism or ejector mechanism is required with the slide cartridge of the present invention. The slide cartridge 1 is simply placed into the chemical analyzer, and after analysis is completed, is removed and properly disposed of, with the used slides remaining therein. The structure of the slide cartridge defines a plurality of reaction chambers 6, and holds each test slide in place in a corresponding reaction chamber. The cooperating rotating upper ring 2 selectively rotates to allow the metering device 68 to deposit a sample fluid on each test slide through the spotter ports 66, and rotates back so that the reaction chamber caps 70 cover the test slide films 20 to ensure that each reaction chamber 6 remains closed at all times once the slides have been spotted.

The preferred embodiment of full, circular upper and lower rings 2, 4 forming the slide cartridge has been described herein. It should, however, be realized that a partial, incomplete ring, such as two curved upper and lower sections of a ring forming an arc or incomplete circle, may be used and may have similar features to those described previously in the preferred ring-shaped slide cartridge.

The slide cartridge preferably accepts 16 test slides, although it is envisioned to be within the scope of this invention to have a slide cartridge which accepts fewer, or more than 16, test slides. If the slide cartridge is structured to accept 16 reagent test slides, then the upper and lower rings need only rotate about 11.25 degrees relative to each other to effect the covering and uncovering (for sample fluid deposition through the spotter ports 66) of the test slides.

The test slides of the present invention cooperate with both the slide cartridge and the chemical analyzer to ensure that they are properly oriented in the slide cartridge and that measurements may be correctly taken by the analyzer. The chemical analyzer works in conjunction with the slide cartridge to maintain the proper temperature of the test slides, rotate the slide cartridge intermittently, and perform the required fluid spotting, reflectance measurements and analysis of the test measurements, and further provide the analysis results to the user on the display 108.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A slide cartridge for use with a chemical analyzer and for holding therein a plurality of reagent test slides, which comprises:
   a first ring; and
   a second ring secured to the first ring, the first and second rings being at least partially rotatable relative to one another, the first ring including a first primary wall, and radially spaced apart inner and outer sidewalls extending perpendicularly from the first primary wall, the first primary wall having a top surface and including ribs protruding upwardly from the top surface, the ribs being spaced apart from one another periodically about the circumference of the first ring, adjacent ribs receiving therebetween a respective reagent test slide of the plurality of reagent test slides, the second ring and the inner and outer sidewalls and ribs of the first ring defining therebetween a plurality of reaction chambers for receiving the plurality of reagent test slides, the reaction chambers being arranged side-by-side circumferentially between the first and second rings and residing in a single plane, the slide cartridge being receivable by a chemical analyzer for testing the plurality of reagent test slides and being removable therefrom after testing of the plurality of reagent test slides has been performed by the chemical analyzer.

2. A slide cartridge as defined by claim 1, wherein the first primary wall of the first ring has formed through the thickness thereof a plurality of viewing windows, each viewing window of the plurality of viewing windows being positioned on the first primary wall in alignment with a respective reaction chamber of the plurality of reaction chambers, a reagent test slide received by a respective reaction chamber being at least partially exposed through a respective viewing window of the plurality of viewing windows.

3. A slide cartridge as defined by claim 1, wherein the first ring has formed therein a plurality of slide insertion openings, each slide insertion opening of the plurality of slide insertion openings being aligned with a respective reaction chamber of the plurality of reaction chambers and being in communication therewith to allow a reagent test slide to pass therethrough and into the respective reaction chamber.

4. A slide cartridge as defined by claim 3, wherein the first ring includes at least one sidewall;
   and wherein the plurality of slide insertion openings are formed through the thickness of the at least one sidewall.

5. A slide cartridge as defined by claim 3, wherein the first primary wall of the first ring includes a plurality of resilient clips, each resilient clip of the plurality of resilient clips being positioned in proximity to a respective slide insertion opening of the plurality of slide insertion openings, each of the resilient clips being engageable with a reagent test slide received by a corresponding reaction chamber to help maintain the reagent test slide within the reaction chamber.

6. A slide cartridge as defined by claim 1, wherein the first ring includes an exposed surface, the exposed surface having formed thereon a circular track of gear teeth.

7. A slide cartridge as defined by claim 1, wherein the second primary wall of the second ring has formed through the thickness thereof a plurality of spaced apart spotter ports, the second ring being rotatable relative to the first ring such that each spotter port of the plurality of spotter ports is selectively positionable in at least partial alignment with a reagent test slide received by a respective reaction chamber of the plurality of reaction chambers.

8. A slide cartridge as defined by claim 1, wherein the second primary wall of the second ring includes a plurality of spaced apart reaction chamber caps, each reaction chamber cap of the plurality of reaction chamber caps being resiliently hinged to the second primary wall and residing in corresponding openings formed through the thickness of the second primary wall, the second ring being rotatable relative to the first ring such that each reaction chamber cap of the plurality of reaction chamber caps is selectively positionable in at least partial alignment with a reagent test slide received by a respective reaction chamber of the plurality of reaction chambers.

9. A slide cartridge as defined by claim 1, wherein the second ring includes a rotation control arm extending from the second primary wall thereof.

10. A slide cartridge as defined by claim 1, wherein adjacent ribs of the first ring are mutually diverging so as to closely receive therebetween a respective reagent test slide having a trapezoidal shape.

11. A slide cartridge for use with a chemical analyzer and for holding therein a plurality of reagent test slides, which comprises:
    a first ring; and
    a second ring secured to the first ring, the first and second rings being at least partially rotatable relative to one another, the first ring including a first primary wall and the second ring including a second primary wall, the first and second rings together defining therebetween a plurality of reaction chambers for receiving the plurality of reagent test slides, the reaction chambers being arranged side-by-side circumferentially between the first and second rings and residing in a single plane, the slide cartridge being receivable by a chemical analyzer for testing the plurality of reagent test slides and being removable therefrom after testing of the plurality of reagent test slides has been performed by the chemical analyzer;
    wherein the first ring has formed therein a plurality of slide insertion openings, each slide insertion opening of the plurality of slide insertion openings being aligned with a respective reaction chamber of the plurality of reaction chambers and being in communication therewith to allow a reagent test slide to pass therethrough and into the respective reaction chamber; and
    wherein the first primary wall of the first ring includes a major portion and deflectable portions resiliently hinged to the major portion, the deflectable portions being situated in alignment with corresponding reaction chambers, the deflectable portions of the first primary wall at least partially defining a respective slide insertion opening of the plurality of slide insertion openings.

12. A slide cartridge for use with a chemical analyzer and for holding therein a plurality of reagent test slides, which comprises:
    a first ring; and
    a second ring secured to the first ring, the first and second rings being at least partially rotatable relative to one another, the first ring including a first primary wall and the second ring including a second primary wall, the first and second rings together defining therebetween a plurality of reaction chambers for receiving the plurality of reagent test slides, the reaction chambers being arranged side-by-side circumferentially between the first and second rings and residing in a single plane, the slide cartridge being receivable by a chemical analyzer for testing the plurality of reagent test slides and being removable therefrom after testing of the plurality of reagent test slides has been performed by the chemical analyzer;

wherein the first ring includes at least one sidewall, the at least one sidewall including a plurality of spaced apart tabs, each tab of the plurality of tabs extending radially from the at least one sidewall into a respective reaction chamber of the plurality of reaction chambers, each tab of the plurality of tabs being partially superposed over the first primary wall and spaced apart therefrom a predetermined distance to allow a reagent test slide to be closely partially received between a corresponding tab and the first primary wall of the first ring.

13. A slide cartridge for use with a chemical analyzer and for holding therein a plurality of reagent test slides, which comprises:

a first ring; and a second ring secured to the first ring, the first and second rings being at least partially rotatable relative to one another, the first ring including a first primary wall and the second ring including a second primary wall, the first and second rings together defining therebetween a plurality of reaction chambers for receiving the plurality of reagent test slides, the reaction chambers being arranged side-by-side circumferentially between the first and second rings and residing in a single plane, the slide cartridge being receivable by a chemical analyzer for testing the plurality of reagent test slides and being removable therefrom after testing of the plurality of reagent test slides has been performed by the chemical analyzer;

wherein the second ring includes a rotation control arm extending from the second primary wall thereof; and wherein the rotation control arm extends through a slot formed in the first ring.

14. A slide cartridge for use with a chemical analyzer and for holding therein a plurality of reagent test slides, which comprises:

a first ring; and a second ring secured to the first ring, the first and second rings being at least partially rotatable relative to one another, the first ring including a first primary wall and the second ring including a second primary wall, the first and second rings together defining therebetween a plurality of reaction chambers for receiving the plurality of reagent test slides, the reaction chambers being arranged side-by-side circumferentially between the first and second rings and residing in a single plane, the slide cartridge being receivable by a chemical analyzer for testing the plurality of reagent test slides and being removable therefrom after testing of the plurality of reagent test slides has been performed by the chemical analyzer;

wherein the first ring further includes first and second sidewalls radially disposed to one another in a spaced apart relationship and mounted on and extending substantially perpendicularly from the first primary wall; and wherein the second ring further includes first and second sidewalls radially disposed to one another in a spaced apart relationship and mounted on and extending substantially perpendicularly from the second primary wall, the second ring being at least partially received by the first ring such that the first and second sidewalls of the second ring are interposed between the first and second sidewalls of the first ring.

15. A slide cartridge as defined by claim 14, wherein at least one of the first and second sidewalls of at least one of the first and second rings includes a plurality of spaced apart resilient clips disposed thereon;

and wherein at least one of the first and second sidewalls of the at least one of the first and second rings includes a plurality of spaced apart, notched out portions which define recessed edges within the notched out portions, the spacing between adjacent resilient clips and the spacing between adjacent notched out portions being substantially the same such that the resilient clips engage the recessed edges defined by the notched out portions when the second ring is partially received by the first ring and secured to the first ring thereby.

16. A slide cartridge for use with a chemical analyzer and for holding therein a plurality of reagent test slides, which comprises:

a first ring; and a second ring secured to the first ring, the first and second rings being at least partially rotatable relative to one another, the first ring including a first primary wall and the second ring including a second primary wall, the first and second rings together defining therebetween a plurality of reaction chambers for receiving the plurality of reagent test slides, the reaction chambers being arranged side-by-side circumferentially between the first and second rings and residing in a single plane, the slide cartridge being receivable by a chemical analyzer for testing the plurality of reagent test slides and being removable therefrom after testing of the plurality of reagent test slides has been performed by the chemical analyzer;

wherein one of the first and second rings includes at least one hooked end mounted thereon, and the other of the first and second rings includes at least one flange mounted thereon, the at least one hooked end engaging the at least one flange to rotatably secure the first ring to the second ring.

17. In combination:

a slide cartridge for use with a chemical analyzer and for holding therein a plurality of reagent test slides, which comprises:

a first ring; and a second ring secured to the first ring, the first and second rings being at least partially rotatable relative to one another, the first ring including a first primary wall, and radially spaced apart inner and outer sidewalls extending perpendicularly from the first primary wall, the first primary wall having a top surface and including ribs protruding upwardly from the top surface, the ribs being spaced apart from one another periodically about the circumference of the first ring, adjacent ribs receiving therebetween a respective reagent test slide of the plurality of reagent test slides, the second ring and the inner and outer sidewalls and ribs of the first ring defining therebetween a plurality of reaction chambers for receiving the plurality of reagent test slides, the reaction chambers being arranged side-by-side circumferentially between the first and second rings and residing in a single plane, the slide cartridge being receivable by a chemical analyzer for testing the plurality of reagent test slides and being removable therefrom after testing of the plurality of reagent test slides has been performed by the chemical analyzer; and a plurality of reagent test slides, each reagent test slide of the plurality of test slides having a film portion carrying a chemical reagent, and a frame surrounding and supporting the film portion, the frame having at least two opposite edges which are non-parallel to each other, the plurality of reagent test slides being received by the slide cartridge such that the at least two opposite non-parallel edges of each reagent test slide are situated in close proximity to respective adjacent ribs of the first primary wall of the first ring, the reagent test slides being arranged side-by-side circumferentially between the first and second rings and residing in a single plane, each reagent test slide of the plurality of reagent test slides being received by a corresponding reaction chamber of the plurality of reaction chambers.

18. A combination as defined by claim 17, wherein adjacent ribs of the lower first ring which receive therebetween a respective reagent test slide extend in a substantially radial direction with respect to the first ring;

and wherein the at least two opposite non-parallel edges of a respective reagent test slide, when received between corresponding adjacent ribs in a corresponding reaction chamber, extend in a substantially radial direction with respect to the first ring.

19. A chemical analyzer for analyzing a plurality of reagent test slides, which comprises:

a reflectometer;

a sample fluid metering device;

a removable slide cartridge carrying a plurality of reagent test slides, the removable slide cartridge having a first ring and a second ring secured to the first ring, the first and second rings being at least partially rotatable relative to one another, the first ring including a first primary wall, and radially spaced, apart inner and outer sidewalls extending perpendicularly from the first primary wall, the first primary wall having a top surface and including ribs protruding upwardly from the top surface, the ribs being spaced apart from one another periodically about the circumference of the first ring, adjacent ribs receiving therebetween a respect reagent test slide of the plurality of reagent test slides, the second ring and the inner and outer sidewalls and ribs of the first ring defining therebetween a plurality of reaction chambers for receiving the plurality of reagent test slides, the reaction chambers being arranged side-by-side circumferentially between the first and second tings and residing in a single plane, the slide cartridge being receivable by the chemical analyzer for testing the plurality of reagent test slides and being removable therefrom after testing of the plurality of reagent test slides has been performed by the chemical analyzer.

20. A chemical analyzer as defined by claim 19, wherein the first ring of the slide cartridge includes an exposed surface having formed thereon a circular track of gear teeth;

and wherein the motor of the chemical analyzer includes a pinion gear operatively coupled thereto, the pinion gear engaging the circular track of gear teeth of the slide cartridge to rotate the slide cartridge.

21. A chemical analyzer as defined by claim 19, wherein the motor is a stepping motor.

* * * * *